(12) United States Patent
Perricone

(10) Patent No.: US 12,364,732 B2
(45) Date of Patent: Jul. 22, 2025

(54) SYSTEMS AND METHODS FOR TREATMENT OF HEARING USING DIHEXA

(71) Applicant: Transdermal Biotechnology, Inc., Meriden, CT (US)

(72) Inventor: Nicholas V. Perricone, Madison, CT (US)

(73) Assignee: Transdermal Biotechnology, Inc., Meriden, CT (US)

( * ) Notice: Subject to any disclaimer, the term of this patent is extended or adjusted under 35 U.S.C. 154(b) by 0 days.

(21) Appl. No.: 18/626,600

(22) Filed: Apr. 4, 2024

(65) Prior Publication Data

US 2024/0424050 A1 Dec. 26, 2024

Related U.S. Application Data

(63) Continuation of application No. 18/339,152, filed on Jun. 21, 2023.

(51) Int. Cl.
| | | |
|---|---|---|
| *A61K 38/04* | (2006.01) | |
| *A61K 9/00* | (2006.01) | |
| *A61K 31/15* | (2006.01) | |
| *A61K 31/385* | (2006.01) | |
| *A61K 31/675* | (2006.01) | |
| *A61K 31/685* | (2006.01) | |
| *A61K 38/10* | (2006.01) | |

(52) U.S. Cl.
CPC .......... *A61K 38/04* (2013.01); *A61K 9/0014* (2013.01); *A61K 9/0046* (2013.01); *A61K 31/15* (2013.01); *A61K 31/385* (2013.01); *A61K 31/675* (2013.01); *A61K 31/685* (2013.01); *A61K 38/10* (2013.01)

(58) Field of Classification Search
None
See application file for complete search history.

(56) References Cited

U.S. PATENT DOCUMENTS

| | | |
|---|---|---|
| 7,182,956 B2 | 2/2007 | Perricone et al. |
| 8,273,711 B2 | 9/2012 | Perricone |
| 8,435,942 B2 | 5/2013 | Perricone et al. |
| 8,668,937 B2 | 3/2014 | Perricone et al. |
| 9,241,899 B2 | 1/2016 | Perricone |
| 9,295,636 B2 | 3/2016 | Perricone |
| 9,295,637 B2 | 3/2016 | Perricone |
| 9,295,647 B2 | 3/2016 | Perricone |
| 9,314,422 B2 | 4/2016 | Perricone |
| 9,314,423 B2 | 4/2016 | Perricone |
| 9,314,433 B2 | 4/2016 | Perricone |
| 9,320,706 B2 | 4/2016 | Perricone |
| 9,320,758 B2 | 4/2016 | Perricone |
| 9,339,457 B2 | 5/2016 | Perricone |
| 9,387,159 B2 | 7/2016 | Perricone |
| 9,687,520 B2 | 6/2017 | Perricone |
| 9,937,227 B2 | 4/2018 | Perricone |
| 10,251,937 B2 * | 4/2019 | Gaudriault .............. A61P 25/24 |
| 11,980,651 B1 * | 5/2024 | Perricone ............... A61K 31/15 |
| 2011/0123577 A1 | 5/2011 | Perricone et al. |
| 2013/0330380 A1 | 12/2013 | Perricone et al. |
| 2014/0271742 A1 | 9/2014 | Perricone |
| 2017/0072013 A1 | 3/2017 | Gaudriault et al. |

FOREIGN PATENT DOCUMENTS

| | | |
|---|---|---|
| CA | 2511849 C | 7/2004 |
| WO | WO 2014/159986 A2 | 10/2014 |
| WO | WO 2014/160016 A2 | 10/2014 |
| WO | WO 2014/160047 A2 | 10/2014 |
| WO | WO 2014/160070 A2 | 10/2014 |
| WO | WO 2014/160102 A2 | 10/2014 |
| WO | WO 2014/160103 A2 | 10/2014 |
| WO | WO 2014/160138 A2 | 10/2014 |

(Continued)

OTHER PUBLICATIONS

Vaseem et al. "Transdermal Drug Delivery Systems: A Focused Review of the Physical Methods of Permeation Enhancement" Advanced Pharmaceutical Bulletin 14:67-85. (Year: 2024).*
Djillani et al., Fighting against depression with TREK-1 blockers: Past and future. A focus on spadin. Pharmacol Ther. Feb. 2019;194:185-198. doi: 10.1016/j.pharmthera.2018.10.003. Epub Oct. 3, 2018.
Djillani et al., Shortened Spadin Analogs Display Better TREK-1 Inhibition, In Vivo Stability and Antidepressant Activity. Front Pharmacol. Sep. 12, 2017;8:643.
Hayes et al., Approaches for peptide and protein cyclisation. Org Biomol Chem. May 12, 2021;19(18):3983-4001.
Lowe, D., Not Alphafold's Fault. Science: In the Pipeline. Sep. 7, 2022. Accessed from <https://www.science.org/content/blog-post/not-alphafold-s-fault>. 6 pages.

(Continued)

Primary Examiner — Sudhakar Katakam
Assistant Examiner — Zachary J Miknis
(74) Attorney, Agent, or Firm — Wolf, Greenfield & Sacks, P.C.

(57) ABSTRACT

The present disclosure generally relates to compositions comprising dihexa and methods for making or using said compositions. In some aspects, the compositions disclosed herein may comprise one or more additional active ingredients, including lipoic acid, spadin peptide, and/or phenyl-N-tert-butylnitrone. Compositions such as these may be used in certain embodiments, for example, to enhances a subject's hearing or to treat a hearing disorder, etc. In some embodiments, the compositions are topical compositions configured to treat hearing loss via administration, e.g., to the skin behind the outer ear or directly to the eardrum of a subject, etc. In some cases, the compositions disclosed herein may comprise one or more excipients to aid in transdermal delivery. For instance, in certain embodiments, the compositions comprise lecithin and/or other components that may facilitate delivery through the skin. Other aspects are generally directed to methods of making or using such compositions, methods of promoting such compositions, kits including such compositions, or the like.

20 Claims, No Drawings
Specification includes a Sequence Listing.

(56) References Cited

FOREIGN PATENT DOCUMENTS

WO    WO 2014/160145 A2    10/2014
WO    WO 2014/160187 A1    10/2014

OTHER PUBLICATIONS

Mazella et al., Spadin, a sortilin-derived peptide, targeting rodent TREK-1 channels: a new concept in the antidepressant drug design. PLoS Biol. Apr. 13, 2010;8(4):e1000355. doi: 10.1371/journal.pbio.1000355.

Mortazavi et al., Skin permeability, a dismissed necessity for anti-wrinkle peptide performance. Int J Cosmet Sci. Apr. 2022;44(2):232-248. doi: 10.1111/ics.12770. Epub Apr. 28, 2022.

Veyssiere et al., Retroinverso analogs of spadin display increased antidepressant effects. Psychopharmacology (Berl). Feb. 2015;232(3):561-74. doi: 10.1007/s00213-014-3683-2. Epub Aug. 2, 2014.

\* cited by examiner

SYSTEMS AND METHODS FOR TREATMENT OF HEARING USING DIHEXA

RELATED APPLICATIONS

This application is a continuation of U.S. patent application Ser. No. 18/339,152, filed Jun. 21, 2023, entitled "Systems and Methods for Treatment of Hearing Using Dihexa," by Nicholas V. Perricone, incorporated herein by reference in its entirety.

REFERENCE TO AN ELECTRONIC SEQUENCE LISTING

The contents of the electronic sequence listing (T067970054US01-SEQ-TC.xml; Size: 72,241 bytes; and Date of Creation: Apr. 3, 2024) is herein incorporated by reference in its entirety.

FIELD

The present disclosure generally relates to systems and methods for delivering a composition comprising dihexa to a subject. In some cases, these may be used for treating hearing loss or other hearing disorders.

BACKGROUND

Hearing loss is usually the result of inner ear or nerve damage. It may be caused by a congenital defect, injury, disease, certain medications, exposure to loud noise, or age-related wear and tear. Hearing loss that is due to damage or death of the hair cells of the inner ear is generally irreversible and is treated with hearing aids, which amplify sounds, or cochlear implants, which bypass damaged portions of the inner ear and directly stimulates the auditory nerve. Unfortunately, current therapies directed toward improving survival and/or regenerating damaged or dead hair cells in the inner ear are limited, with only one drug being approved over the past decade (e.g., PEDMARK for pediatric cisplatin-associated ototoxicity). Thus, improvements are needed.

SUMMARY

The present disclosure generally relates to systems and methods for delivering a composition comprising dihexa to a subject. The subject matter of the present disclosure involves, in some cases, interrelated products, alternative solutions to a particular problem, and/or a plurality of different uses of one or more systems and/or articles.

Aspects of the disclosure generally relate to one or more compositions for transdermal delivery. In some embodiments, the compositions for delivery to the ear is disclosed. In some cases, the composition comprises a topical formulation comprising dihexa, lipoic acid, spadin peptide, and phenyl-N-tert-butylnitrone.

In other embodiments, the compositions comprise a topical formulation comprising dihexa and lipoic acid and lecithin.

In some instances, the compositions comprise a topical formulation comprising dihexa and spadin peptide and lecithin.

In yet other cases, still, the compositions comprise a topical formulation comprising dihexa and phenyl-N-tert-butylnitrone and lecithin.

Other aspects of the disclosure relate to one or more methods for delivery said compositions. For instance, in some embodiments, the methods comprise applying, to the ear of a subject, a pharmaceutical composition comprising dihexa, lipoic acid, spadin peptide, and phenyl-N-tert-butylnitrone.

In other embodiments, the method is a method for treating hearing loss in a subject. The methods, in some cases, may comprise administering a therapeutic amount of a composition comprising (i) dihexa and (ii) a alpha-lipoic acid, or a derivative thereof, to the ear of a subject. In some embodiments, the alpha-lipoic acid enhances the therapeutic effect of the dihexa.

In some embodiments, the methods comprise administering a therapeutic amount of a composition comprising (i) dihexa and (ii) a spadin peptide or a retroinverso analog of a spadin peptide, to the ear of the subject, wherein the retroinverso analog enhances the therapeutic effect of the dihexa.

In other embodiments, still, the methods comprise administering a therapeutic amount of a composition to a subject diagnosed with hearing loss, wherein the composition comprises dihexa, or a derivative thereof, a lipoic acid, or a derivative thereof, a spadin peptide, or a derivative thereof, and a phenyl-N-tert-butylnitrone, or a derivative thereof.

In another aspect, the present disclosure encompasses methods of making one or more of the embodiments described herein. In still another aspect, the present disclosure encompasses methods of using one or more of the embodiments described herein.

Other advantages and novel features of the present disclosure will become apparent from the following detailed description of various non-limiting embodiments of the disclosure.

DETAILED DESCRIPTION

The present disclosure generally relates to compositions comprising dihexa and methods for making or using said compositions. In some aspects, the compositions disclosed herein may comprise one or more additional active ingredients, including lipoic acid, spadin peptide, and/or phenyl-N-tert-butylnitrone. Compositions such as these may be used in certain embodiments, for example, to enhances a subject's hearing or to treat a hearing disorder, etc. In some embodiments, the compositions are topical compositions configured to treat hearing loss via administration, e.g., to the skin behind the outer ear or directly to the eardrum of a subject, etc. In some cases, the compositions disclosed herein may comprise one or more excipients to aid in transdermal delivery. For instance, in certain embodiments, the compositions comprise lecithin and/or other components that may facilitate delivery through the skin. Other aspects are generally directed to methods of making or using such compositions, methods of promoting such compositions, kits including such compositions, or the like.

In some embodiments, compositions comprising dihexa, and one or more additional active ingredients, may provide one or more health benefits for subjects with hearing loss or other hearing disorders. In some cases, such compositions may exhibit rapid onset times and/or may not induce undesirable side effects in some cases. For example, in some embodiments, treatment with the compositions disclosed herein may improve hair cell function or induce hair cell regeneration without inducing insomnia, indigestion, dizziness, headaches, etc. As such, some of the compositions disclosed herein may be useful for improving hearing loss that is sensorineural (e.g., caused by dysfunction in the cochlea or spiral ganglion)

Dihexa is an art-recognized oligopeptide drug derived from angiotensin IV that binds with high affinity to hepatocyte growth factor (HGF) and potentiates its activity at its receptor, c-Met. HGF is believed to stimulate cell proliferation, cell dispersion, neuronal survival, and wound healing, among other. For example, in the inner ear, levels of HGF may be fine-tuned for normal hearing.

As used herein, the term "dihexa" is synonymous with PNB-0408, N-hexanoic-Tyr-Ile-(6) aminohexanoic amide, and N-(1-Oxohexyl)-L-tyrosyl-N-(6-amino-6-oxohexyl)-L-isolucinamide. In some embodiments, dihexa has the following structure:

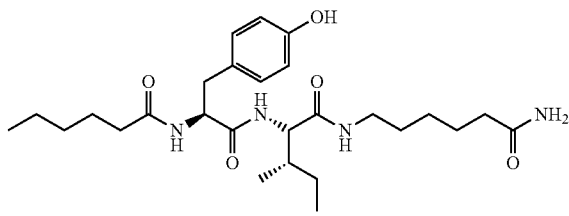

In some embodiments, dihexa may be a functional derivative of the above structure. Without wishing to be bound by any particular theory, dihexa is an art-recognized HGF mimic that possesses improved chemical stability and blood-brain barrier permeability relative to HGF itself. Dihexa functions by dimerizing with endogenous HGF to activate the HGF receptor and downstream signaling cascades. Dihexa has been found to potently improve cognitive function in animal models of Alzheimer's disease-like mental impairment and to protect hair cells from chemical ototoxicity.

Dihexa, or any functional derivative thereof, may be present at any suitable amount within the composition. In some embodiments, the dihexa is present in the composition between about 0.25 wt % and 50 wt %, between 0.25 wt % and 75 wt %, or between 0.25 wt % and 90 wt %.

In some embodiments, the composition is at least about 0.25 wt %, at least about 0.5 wt %, at least about 1 wt %, at least about 2 wt %, at least about 3 wt %, at least about 5 wt %, at least about 8 wt %, at least about 10 wt %, at least about 20 wt %, at least about 30 wt %, at least about 40 wt %, at least about 50 wt %, at least about 60 wt %, at least about 70 wt %, at least about 80 wt %, or at least about 90 wt % of the entire composition can be the dihexa or any functional derivative thereof. In some cases, the dihexa, or any functional derivative thereof, may be present at a concentration of no more than about 95 wt %, no more than about 90 wt %, no more than about 80 wt %, no more than about 70 wt %, no more than about 65 wt %, no more than about 60 wt %, no more than about 50 wt %, no more than about 40 wt %, no more than about 30 wt %, no more than about 20 wt %, or no more than about 10%. Combinations of any of these are also possible. For instance, the dihexa, or any functional derivative thereof, may be present at between about 8 wt % and about 65 wt %, or between about 0 wt % and about 10 wt %, etc.

It has now been discovered that combining dihexa with one or more additional active ingredients, discussed in more detail below, may improve the health of damaged or dying hair cells and/or stimulates regeneration of new hair cells within the middle ear. For example, in some embodiments, the compositions comprise dihexa and alpha-lipoic acid. In other embodiments, the compositions comprise dihexa and spadin peptide. In other embodiments still, the compositions comprise dihexa and phenyl-N-tert-butylnitrone. Other embodiments include compositions comprising dihexa, lipoic acid, spadin peptide, and phenyl-N-tert-butylnitrone. Other combinations are possible in other embodiments, e.g., compositions comprising dihexa, lipoic acid, and spadin peptide, compositions comprising dihexa, lipoic acid, and phenyl-N-tert-butylnitrone, and compositions comprising dihexa, spadin peptide, and phenyl-N-tert-butylnitrone.

In some embodiments, the compositions disclosed herein further comprise lipoic acid. As used herein, the term "lipoic acid" is synonymous with lipoate, alpha-lipoic acid, α-lipoic acid, LA, ALA, and thioctic acid. Lipoic acid is an organosulfur compound that is biosynthetically derived from caprylic acid (octanoic acid, e.g., via normal biosynthesis). Additionally, lipoic acid, or its conjugate base, may be chemically synthesized by those of skill in the art, and administered to a subject in need (e.g., via consumption or transdermal delivery). In some embodiments, lipoic acid has the following structure:

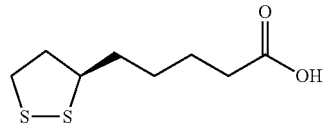 [SMILES: O=C(O)CCCC[C@@H]1CCSS1]

In some embodiments, lipoic acid may be a functional derivative of the above structure. As mentioned above, lipoate is the conjugate base of lipoic acid and is the most prevalent form of lipoic acid under physiological conditions. Importantly, only the (R)-(+)-enantiomer (RLA) exists in nature, as this isomer is a cofactor that is essential to the function of several enzymes, e.g., pyruvate dehydrogenase, a-ketoglutarate dehydrogenase, the glycine cleavage system, branched chain keto acid dehydrogenase, and the alpha-oxo (keto) adipate dehydrogenase, some which are involved in aerobic respiration.

Without wishing to be bound by any particular theory, it is believed that lipoic acid may stimulate nerve growth factor synthesis. This activity is believed to be due to its oxidative and/or reductive activity.

The lipoic acid, or functional derivative thereof, may be present at any suitable amount within the composition. In some embodiments, lipoic acid is present in the composition between about 0.25 wt % and 50 wt %, between 0.25 wt % and 75 wt %, or between 0.25 wt % and 90 wt %. In some embodiments, the lipoic acid is present at least about 0.25 wt %, at least about 0.5 wt %, at least about 1 wt %, at least about 2 wt %, at least about 3 wt %, at least about 5 wt %, at least about 8 wt %, at least about 10 wt %, at least about 20 wt %, at least about 30 wt %, at least about 40 wt %, at least about 50 wt %, at least about 60 wt %, at least about 70 wt %, at least about 80 wt %, or at least about 90 wt % of the entire composition may be lipoic acid, or any functional derivative thereof. In some cases, the lipoic acid, or any functional derivative thereof, may be present at a concentration of no more than about 95 wt %, no more than about 90 wt %, no more than about 80 wt %, no more than about 70 wt %, no more than about 65 wt %, no more than about 60 wt %, no more than about 50 wt %, no more than about 40 wt %, no more than about 30 wt %, no more than about 20 wt %, or no more than about 10%. Combinations of any of these are also possible. For instance, the lipoic acid, or functional derivative thereof, may be present at between about 8 wt % and about 65 wt %, or between about 0 wt % and about 10 wt %, etc.

In some embodiments, the compositions disclosed herein further comprise spadin peptide. Spadin peptides are art-recognized peptides that are derived from a sortilin protein. Sortilin is derived from prosortilin which is cleaved by a protein convertase furin during post-translational processing into mature sortilin and a 44-amino acid peptide named propeptide PE (1-44). As used herein, the term "spadin peptide" refers to propeptide PE (1-44) or any fragment thereof. For example, in some embodiments, the spadin peptide is propeptide PE (1-44) with amino acid sequence NH$_2$-QDRLDAPPPPAAPLPRWSGPIGVSWGL-RAAAAGGAFPRGGOURWRR-COOH (SEQ ID NO: 1, PE-1-44). The spadin peptide may also be any fragment of SEQ ID NO: 1, according to other embodiments. Exemplary fragments include, but are not limited to NH$_2$-APLPRWSG-PIGVSWGLR-COOH (SEQ ID NO: 3, PE-12-28, Analog 2), NH$_2$-QDRLDAPPPPAAPLPRWSGPIGVSWGLR-COOH (SEQ ID NO: 10, Analog 9, PE-1-28), NH$_2$-GVSWGLR-COOH (SEQ ID NO: 12, Analog 11, PE-22-28), NH$_2$-IGVSWGLR-COOH (SEQ ID NO: 16, Analog 15, PE-21-28), NH$_2$-APPPPAAPLPRWSGPIGVSWGLR-COOH (SEQ ID NO: 18, Analog 17, PE-6-28), NH$_2$-APLPRWSGPIGVSWGL-COOH (SEQ ID NO: 20, Analog 19, PE-12-27), NH$_2$-LPRWSGPIGVSW-COOH (SEQ ID NO: 22, Analog 21, PE-14-25), NH$_2$-GVSW-COOH (SEQ ID NO: 24, Analog 23, PE-22-25), and NH$_2$-GVSWGL-COOH (SEQ ID NO: 25, Analog 24, PE-22-27). Other fragments are also contemplated in other embodiments.

The spadin peptide, or any fragment thereof, may be a retro-inverso peptide in some embodiments. As used herein, the term "retro-inverso peptide" refers to a peptide whose amino acid sequence is reversed, and the alpha-center chirality of the amino acid subunits is inverted. Thus, in some embodiments, the amino acid is an L-amino acid; in other embodiments, the amino acid is a D-amino acid. As used herein, L-amino acids are represented by capital letters within an amino acid sequence and D-amino acids are represented by lower-case letters within an amino acid sequence. For example, in some embodiments, the retro-inverso spadin peptide is a retro-inverso peptide of propeptide PE (1-44) with amino acid sequence NH$_2$-rrwrGGrpf-aGGaaaarlGwsvGipGswrplpaappppadlrdq-Ac (SEQ ID NO: 2, Analog 1, retroinverso of propeptide PE 1-44). Other exemplary retro-inverso spadin peptides are also contemplated in other embodiments. For instance, in some embodiments, the retro-inverso peptide is a retro-inverso peptide of Analog 2 with amino acid sequence NH$_2$-rlGwsvGipGswr-plpa-Ac (SEQ ID NO: 5, Analog 4). Other exemplary retro-inverso spadin peptides, or fragments thereof, include, but are not limited to, a retro-inverso peptide of Analog 5 with amino acid sequence NH$_2$-rlawsvaipaswrplpa-COOH (SEQ ID NO: 7, Analog 6), a retro-inverso peptide of Analog 9 with amino acid sequence NH$_2$-rlGwsvGipGswrplpaappp-padlrdq-Ac (SEQ ID NO: 11, Analog 10), a retro-inverso peptide of Analog 15 with amino acid sequence NH$_2$-rlGwsvGi-Ac (SEQ ID NO: 17, Analog 16), a retro-inverso peptide of Analog 17 with amino acid sequence NH$_2$-rlGwsvGipGswrplpaappppa-Ac (SEQ ID NO: 19, Analog 18), a retro-inverso peptide of Analog 19 with amino acid sequence NH$_2$-IGwsvGipGswrplpa-Ac (SEQ ID NO: 21, Analog 20), or a retro-inverso peptide of Analog 21 with amino acid sequence NH$_2$-wsvGIpGswrpl-Ac (SEQ ID NO: 23, Analog 22). Other retro-inverso spadin peptide, or fragments thereof, are also contemplated in other embodiments.

Additionally, or alternatively, a spadin peptide, or any fragment thereof, may comprise one or more tags. As used herein, the term "tag" refers to moiety capable of being grafted to the spadin peptide, or any fragment thereof. Any suitable tag known in the art capable of being grafted onto the spadin peptide, or any fragment thereof, is contemplated herein. Exemplary embodiments include, but are not limited to, peptide/protein tags, affinity tags (e.g., biotin-tag, avidin-tag, chitin binding protein/CBP, maltose binding protein/MBP, strep-tag, glutathione-S-transferase/GST, poly(His), etc.), solubilization tags (e.g., thioredoxin/TRX, poly (NANP), etc.), chromatography tags (e.g., FLAG, polyglutamate, etc.), epitope tags (ALFA-tag, V5-tag, Myc-tag, HA-tag, Spot-tag, T7-tag, NE-tag, etc.), fluorescence tags (green fluorescent protein, alexa fluor dyes, or the like, etc.), and nucleic acid tags (e.g., RNAs, miRNAs, siRNAs, DNA, etc.). Other tags are contemplated in other embodiments. Combinations of tags are also possible (e.g., solubilization and fluorescent tag).

In certain embodiments, a spadin peptide, or any fragment thereof, comprises one or more amino acid substitutions. According to one set of embodiments, an amino acid located at any position within an amino acid sequence of a spadin peptide, or fragment thereof, may be substituted with a different amino acid at the same position. For example, in some embodiments, the one or more amino acids are substituted at a single position within the amino acid sequence (e.g., at position 5 in an amino acid sequence having positions 1-20). In other embodiments, the one or more amino acids are inserted at multiple positions within the amino acid sequence (e.g., at positions 5 and 10 in an amino acid sequence having positions 1-20).

Any amino acid, or combination of amino acids, (e.g., naturally occurring and/or synthetically derived) may be used in any of the spadin peptides, or fragments thereof, disclosed herein. Natural and/or non-natural amino acids may be synthesized using art recognized techniques or obtained by purchase from a commercial vendor (e.g., MilliPore Sigma, JPT, Anaspec, etc.). Exemplary embodiments of naturally occurring amino acids include, but are not limited to, arginine (R) histidine (H), lysine (K), aspartic acid (D), glutamic acid (E), serine(S), threonine (T), asparagine (N), glutamine (Q), cysteine (C), selenocysteine (U), glycine (G), proline (P), alanine (A), valine (V), isoleucine (I), leucine (L), methionine (M), phenylalanine (F), tyrosine (Y), and tryptophan (W).

Exemplary embodiments of non-natural amino acids include, but are not limited to, D-amino acids (e.g., mirror image of naturally occurring L-isomer), homo-amino acids (e.g., naturally occurring amino acid comprising a methylene group to the alpha carbon), beta-homo-amino acids (e.g., analogs of naturally occurring amino acids in which the carbon skeleton has been lengthened by insertion of one carbon atom immediately after the acid group), N-methyl amino acids (e.g., analogs of naturally occurring amino acids that carry a methyl group at the amide nitrogen adjacent the alpha carbon instead of a proton), alpha-methyl amino acids (e.g., analog of naturally occurring amino acids in which the proton on the alpha-carbon is substituted by a methyl group), and unusual amino acids (e.g., citrulline (Cit), hydroxyproline (Hyp), norleucine (Nle), 3-nitrotyrosine, nitroarginine, ornithine (Orn), naphtylalanine (Nal), Abu, DAB, methionine sulfoxide, or methionine sulfone. Other non-natural amino acids are also possible in other embodiments, for example, beta-2 amino acids, beta-3 amino acids, beta-3 homo amino acids, ACHC, and peptoids, among others.

In another set of embodiments, one or more amino acids may be inserted into an amino acid sequence of a spadin peptide, or fragment thereof. In some embodiments, the one or more amino acids are inserted at a single position within the amino acid sequence (e.g., at position 5 in an amino acid sequence having positions 1-20). In other embodiments, the one or more amino acids are inserted at multiple positions within the amino acid sequence (e.g., at positions 5 and 10 in an amino acid sequence having positions 1-20).

In an additional set of embodiments, one or more amino acids may be deleted from an amino acid sequence of a spadin peptide, or fragment thereof. In some embodiments, the one or more amino acids are deleted at a single position within the amino acid sequence (e.g., at position 5 in an amino acid sequence having positions 1-20). In other embodiments, the one or more amino acids are deleted from multiple positions within the amino acid sequence (e.g., at positions 5 and 10 in an amino acid sequence having positions 1-20).

In some embodiments, the spadin peptide, or any fragment thereof, is linear. In other embodiments, the spadin peptide, or any fragment thereof, is circular (e.g., it has been cyclized). Any method known in the art may be used to cyclize any of the spadin peptides, or fragments thereof. For example, in some embodiments, the spadin peptide, or any fragment thereof, is cyclized via side chain-to-side change cyclization (e.g., conjugation between the side chain primary amino group of lysine and the side change carboxylic acid group of glutamic acid), head-to-tail cyclization (e.g., conjugation between the carboxylic acid group at the C-terminal end of the peptide and the primary amino group at the N-terminal end of the peptide), tail-to-side chain cyclization (e.g., conjugation between the carboxylic acid group at the C-terminal end of the peptide and the side chain primary amino group of lysine), and head-to-side chain cyclization (e.g., conjugation between the primary amino group at the N-terminal end of the peptide and the side change carboxylic acid group of glutamic acid). In one set of embodiments, cyclization is accomplished using disulfide bonds (e.g., between two cysteine amino acids) positioned at or near the N-terminus and at or near the C-terminus.

Other cyclization strategies are also possible in other embodiments. For example, in some embodiments, native chemical ligation (NCL) may be used to conjugate a first end of a peptide to a second end of the same peptide (e.g., to cyclize the peptide). In another set of embodiments, cyclization may be accomplished by conjugating the N-terminal amine group and a C-terminal aldehyde group. Additional embodiments include, for example, biorthogonal reactions, such as traceless Staudinger ligation, type II alpha-ketoacid-hydroxylamine (KAHA) ligation, 2((alkylthio)(aryl)methylene)malononitrile (TAMM) condensation and cycloaddition reactions (e.g., copper catalyzed, strain-induced copper free, etc.).

In some cases, non-chemical methods (e.g., enzymatic methods) may also be used to cyclize the spadin peptide, or any fragment thereof. In some embodiments, cyclization is accomplished enzymatically. Any enzyme known in the art capable of cyclizing a spadin peptide, or any fragment thereof, is contemplated herein. Exemplary embodiments include, but are not limited to, subtiligase variants (e.g., a double mutant of the serine protease subtilisin BPN' from Bacillus amyloliquefaciens), sortases (e.g., cysteine transpeptidases), asparaginyl endopeptidases (e.g., cysteine proteases such as Butelase 1, OaAEP1, HaAEP1, MCoAEP2, VyPAL1-2, etc.), transglutaminase (e.g., catalyze an acyl transfer reaction between the carboxyamide group of glutamine residues and various primary amines, including the epsilon-amino group of lysine).

In some embodiments, a spadin peptide, or any fragment thereof, may be synthesized using any technique known to those of skill in the art. For example, in some cases, the spadin peptide, or any fragment thereof, is synthesized chemically using synthetic techniques such as solution phase peptide chemistry, solid phase peptide synthesis (SPPS), or the like. Without wishing to be bound by any particular theory, synthetic techniques for peptide synthesis are based on the concept that peptides may be assembled by via a series of sequential coupling reactions between the primary amine functionality of an N-terminus of a first amino acid and a carboxylic acid functionality of a C-terminus of a second adjacent amino acid. In some embodiments, the amino acid building blocks may further comprise removable protecting groups conjugated to the C-terminal carboxyl group, the N-terminal amino group, or a reactive group in the side chain group (e.g., an $NH_2$, COOH, SH, etc.). Exemplary protecting groups are generally known by those of skill in the art, and include 9-fluorenylmethoxycarbonyl (FMOC) groups (e.g., for protection of N-terminal primary amine groups), tert-butylocycarbonyl groups (BOC) groups (e.g., for protection of side chain groups in Lysine, Tryptophan, etc.), tert-butyl (tBu) groups (e.g., for protection of side chain groups in glutamic acid, aspartic acid, etc.), 2,2,4,6,7-pentamethyl-dihydrobenzofuran-5-sulfonyl (Pfb) groups (e.g., for protection of side chain groups in arginine), trityl (Trt) groups (e.g., for protection of side chain groups in cystine, histidine, and glutamine). Other protecting groups are possible in other embodiments. Other synthetic routes are also possible in some embodiments.

As an example, in some embodiments, a spadin peptide, or any fragment thereof, is synthesized using genetic engineering techniques. For example, in some cases, a polynucleotide encoding the sequence of the spadin peptide, or any fragment thereof, may be inserted into a plasmid/vector and transfected (e.g., non-virally mediated)/transduced (e.g., virus-mediated) into a cell. The cell may be a plant cell, a mammalian cell, a bacterial cell, or an insect cell. In some embodiments, the expression of the polynucleotide is operably linked to a promoter. The promoter may be an inducible promoter or a constitutively active promoter. In some embodiments, the polynucleotide encoding the gene encoding the spadin peptide, or any fragment thereof, may further encode a tag sequence, for example, to aid in purification. Any tag sequence known in the art may be used, for example, 6×His tag. In some embodiments, the tag sequence is cleavable from construct comprising the spadin peptide, or any fragment thereof. Those of ordinary skill in the art will be generally familiar with common genetic engineering techniques such as the use of plasmids, transfection, and the like.

In other cases, a spadin peptide, or any fragment thereof, is synthesized using non-ribosomal peptide synthesis (NPRS). Without wishing to be bound by theory NPRS are large multifunctional enzymes that assemble one type of polypeptide without the need for cell ribosomal machinery and messenger RNAs. Each module of the NRPS is responsible for the incorporation of a specific amino acid building block. In some embodiments, the NRPS comprises an adenylation (A) domain, a thiolation (T) domain, and a condensation (C) domain. The A domain activates a specific amino acid by transesterification with ATP to generate the corresponding aminoacyl-adenylate. The T domain tethers the aminoacyl-adenylate to the enzyme through the formation of thioester linkage. The C domain catalyzes the formation of a peptide bond between the activated acyl group and the free amino group of an amino acid on the neighboring module. The peptide chain grows in the N-to-C terminal direction until it is release by a thioesterase (TE) domain (e.g., through hydrolysis, oligomerization, or cyclization).

In some embodiments, the spadin peptide, or any fragment thereof, has an amino acid sequence that is at least 85%, at least 90%, at least 95%, or at least 98% identical to the amino acid sequence of SEQ ID NO: 1 (Propeptide PE 1-44). In some embodiments, the spadin peptide, or any fragment thereof, has an amino acid sequence that is at least 85%, at least 90%, at least 95%, at least 98% identical to the amino acid sequence of SEQ ID NO: 2 (Analog 1). In some embodiments, the spadin peptide, or any fragment thereof, has an amino acid sequence that is at least 85%, at least 90%, at least 95%, or at least 98% identical to the amino acid sequence of SEQ ID NO: 3 (Analog 2). In some embodiments, the spadin peptide, or any fragment thereof, has an amino acid sequence that is at least 85%, at least 90%, at least 95%, or at least 98% identical to the amino acid sequence of SEQ ID NO: 4 (Analog 3). In some embodiments, the spadin peptide, or any fragment thereof, has an amino acid sequence that is at least 85%, at least 90%, at least 95%, or at least 98% identical to the amino acid sequence of SEQ ID NO: 5 (Analog 4). In some embodiments, the spadin peptide, or any fragment thereof, has an amino acid sequence that is at least 85%, at least 90%, at least 95%, or at least 98% identical to the amino acid sequence of SEQ ID NO: 6 (Analog 5). In some embodiments, the spadin peptide, or any fragment thereof, has an amino acid sequence that is at least 85%, at least 90%, at least 95%, or at least 98% identical to the amino acid sequence of SEQ ID NO: 7 (Analog 6). In some embodiments, the spadin peptide, or any fragment thereof, has an amino acid sequence that is at least 85%, at least 90%, at least 95%, or at least 98% identical to the amino acid sequence of SEQ ID NO: 8 (Analog 7). In some embodiments, the spadin peptide, or any fragment thereof, has an amino acid sequence that is at least 85%, at least 90%, at least 95%, or at least 98% identical to the amino acid sequence of SEQ ID NO: 9 (Analog 8). In some embodiments, the spadin peptide, or any fragment thereof, has an amino acid sequence that is at least 85%, at least 90%, at least 95%, or at least 98% identical to the amino acid sequence of SEQ ID NO: 10 (Analog 9). In some embodiments, the spadin peptide, or any fragment thereof, has an amino acid sequence that is at least 85%, at least 90%, at least 95%, or at least 98% identical to the amino acid sequence of SEQ ID NO: 11 (Analog 10). In some embodiments, the spadin peptide, or any fragment thereof, has an amino acid sequence that is at least 85%, at least 90%, at least 95%, or at least 98% identical to the amino acid sequence of SEQ ID NO: 12 (Analog 11). In some embodiments, the spadin peptide, or any fragment thereof, has an amino acid sequence that is at least 85%, at least 90%, at least 95%, or at least 98% identical to the amino acid sequence of SEQ ID NO: 13 (Analog 12). In some embodiments, the spadin peptide, or any fragment thereof, has an amino acid sequence that is at least 85%, at least 90%, at least 95%, or at least 98% identical to the amino acid sequence of SEQ ID NO: 14 (Analog 13). In some embodiments, the spadin peptide, or any fragment thereof, has an amino acid sequence that is at least 85%, at least 90%, at least 95%, or at least 98% identical to the amino acid sequence of SEQ ID NO: 15 (Analog 14). In some embodiments, the spadin peptide, or any fragment thereof, has an amino acid sequence that is at least 85%, at least 90%, at least 95%, or at least 98% identical to the amino acid sequence of SEQ ID NO: 16 (Analog 15). In some embodiments, the spadin peptide, or any fragment thereof, has an amino acid sequence that is at least 85%, at least 90%, at least 95%, or at least 98% identical to the amino acid sequence of SEQ ID NO: 17 (Analog 16). In some embodiments, the spadin peptide, or any fragment thereof, has an amino acid sequence that is at least 85%, at least 90%, at least 95%, or at least 98% identical to the amino acid sequence of SEQ ID NO: 18 (Analog 17). In some embodiments, the spadin peptide, or any fragment thereof, has an amino acid sequence that is at least 85%, at least 90%, at least 95%, or at least 98% identical to the amino acid sequence of SEQ ID NO: 19 (Analog 18). In some embodiments, the spadin peptide, or any fragment thereof, has an amino acid sequence that is at least 85%, at least 90%, at least 95%, or at least 98% identical to the amino acid sequence of SEQ ID NO: 20 (Analog 19). In some embodiments, the spadin peptide, or any fragment thereof, has an amino acid sequence that is at least 85%, at least 90%, at least 95%, or at least 98% identical to the amino acid sequence of SEQ ID NO: 21 (Analog 20). In some embodiments, the spadin peptide, or any fragment thereof, has an amino acid sequence that is at least 85%, at least 90%, at least 95%, or at least 98% identical to the amino acid sequence of SEQ ID NO: 22 (Analog 21). In some embodiments, the spadin peptide, or any fragment thereof, has an amino acid sequence that is at least 85%, at least 90%, at least 95%, or at least 98% identical to the amino acid sequence of SEQ ID NO: 23 (Analog 22). In some embodiments, the spadin peptide, or any fragment thereof, has an amino acid sequence that is at least 85%, at least 90%, at least 95%, or at least 98% identical to the amino acid sequence of SEQ ID NO: 24 (Analog 23). In some embodiments, the spadin peptide, or any fragment thereof, has an amino acid sequence that is at least 85%, at least 90%, at least 95%, or at least 98% identical to the amino acid sequence of SEQ ID NO: 25 (Analog 24).

In some embodiments, the spadin peptide, or any fragment thereof, has an amino acid sequence that has no more than 1 amino acid substitutions, no more than 2 amino acid substitutions, or no more than 3 amino acid substitutions from the amino acid sequence of SEQ ID NO: 1 (Propeptide PE 1-44). In some embodiments, the spadin peptide, or any fragment thereof, has an amino acid sequence that has no more than 1 amino acid substitutions, no more than 2 amino acid substitutions, or no more than 3 amino acid substitutions from SEQ ID NO: 2 (Analog 1). In some embodiments, the spadin peptide, or any fragment thereof, has an amino acid sequence that has no more than 1 amino acid substitutions, no more than 2 amino acid substitutions, or no more than 3 amino acid substitutions from SEQ ID NO: 3 (Analog 2). In some embodiments, the spadin peptide, or any fragment thereof, has an amino acid sequence that has no more than 1 amino acid substitutions, no more than 2 amino acid substitutions, or no more than 3 amino acid substitutions from SEQ ID NO: 4 (Analog 3). In some embodiments, the spadin peptide, or any fragment thereof, has an amino acid sequence that has no more than 1 amino acid substitutions, no more than 2 amino acid substitutions, or no more than 3 amino acid substitutions from SEQ ID NO: 5 (Analog 4). In some embodiments, the spadin peptide, or any fragment thereof, has an amino acid sequence that has no more than 1 amino acid substitutions, no more than 2 amino acid substitutions, or no more than 3 amino acid substitutions from SEQ ID NO: 6 (Analog 5). In some embodiments, the spadin peptide, or any fragment thereof, has an amino acid sequence that has no more than 1 amino acid substitutions, no more than 2 amino acid substitutions, or no more than 3 amino acid substitutions from SEQ ID NO: 7 (Analog 6). In some embodiments, the spadin peptide, or any fragment thereof, has an amino acid sequence that has no more than 1 amino acid substitutions, no more than 2 amino acid substitutions, or no more than 3 amino acid substitutions from SEQ ID NO: 8 (Analog 7). In some embodiments, the spadin peptide, or any fragment thereof, has an amino acid sequence that has no more than 1 amino acid substitutions, no more than 2 amino acid substitutions, or no more than 3 amino acid substitutions from SEQ ID NO: 9 (Analog 8). In some embodiments, the spadin peptide, or any fragment thereof, has an amino acid sequence that has no more than 1 amino acid substitutions, no more than 2 amino acid substitutions, or no more than 3 amino acid substitutions from SEQ ID NO: 10 (Analog 9). In some embodiments, the spadin peptide, or any fragment thereof, has an amino acid sequence that has no more than 1 amino acid substitutions, no more than 2 amino acid substitutions, or no more than 3 amino acid substitutions from SEQ ID NO: 11 (Analog 10). In some embodiments, the spadin peptide, or any fragment thereof, has an amino acid sequence that has no more than 1 amino acid substitutions, no more than 2 amino acid substitutions, or no more than 3 amino acid substitutions from SEQ ID NO: 12 (Analog 11). In some embodiments, the spadin peptide, or any fragment thereof, has an amino acid sequence that has no more than 1 amino acid substitutions, no more than 2 amino acid substitutions, or no more than 3 amino acid substitutions from SEQ ID NO: 13 (Analog 12).

In some embodiments, the spadin peptide, or any fragment thereof, has an amino acid sequence that has no more than 1 amino acid substitutions, no more than 2 amino acid substitutions, or no more than 3 amino acid substitutions from SEQ ID NO: 14 (Analog 13). In some embodiments, the spadin peptide, or any fragment thereof, has an amino acid sequence that has no more than 1 amino acid substitutions, no more than 2 amino acid substitutions, or no more than 3 amino acid substitutions from SEQ ID NO: 15 (Analog 14). In some embodiments, the spadin peptide, or any fragment thereof, has an amino acid sequence that has no more than 1 amino acid substitutions, no more than 2 amino acid substitutions, or no more than 3 amino acid substitutions from SEQ ID NO: 16 (Analog 15). In some embodiments, the spadin peptide, or any fragment thereof, has an amino acid sequence that has no more than 1 amino acid substitutions, no more than 2 amino acid substitutions, or no more than 3 amino acid substitutions from SEQ ID NO: 17 (Analog 16). In some embodiments, the spadin peptide, or any fragment thereof, has an amino acid sequence that has no more than 1 amino acid substitutions, no more than 2 amino acid substitutions, or no more than 3 amino acid substitutions from SEQ ID NO: 18 (Analog 17). In some embodiments, the spadin peptide, or any fragment thereof, has an amino acid sequence that has no more than 1 amino acid substitutions, no more than 2 amino acid substitutions, or no more than 3 amino acid substitutions from SEQ ID NO: 19 (Analog 18). In some embodiments, the spadin peptide, or any fragment thereof, has an amino acid sequence that has no more than 1 amino acid substitutions, no more than 2 amino acid substitutions, or no more than 3 amino acid substitutions from SEQ ID NO: 20 (Analog 19). In some embodiments, the spadin peptide, or any fragment thereof, has an amino acid sequence that has no more than 1 amino acid substitutions, no more than 2 amino acid substitutions, or no more than 3 amino acid substitutions from SEQ ID NO: 21 (Analog 20). In some embodiments, the spadin peptide, or any fragment thereof, has an amino acid sequence that has no more than 1 amino acid substitutions, no more than 2 amino acid substitutions, or no more than 3 amino acid substitutions from SEQ ID NO: 22 (Analog 21). In some embodiments, the spadin peptide, or any fragment thereof, has an amino acid sequence that has no more than 1 amino acid substitutions, no more than 2 amino acid substitutions, or no more than 3 amino acid substitutions from SEQ ID NO: 23 (Analog 22). In some embodiments, the spadin peptide, or any fragment thereof, has an amino acid sequence that has no more than 1 amino acid substitutions, no more than 2 amino acid substitutions, or no more than 3 amino acid substitutions from SEQ ID NO: 24 (Analog 23). In some embodiments, the spadin peptide, or any fragment thereof, has an amino acid sequence that has no more than 1 amino acid substitutions, no more than 2 amino acid substitutions, or no more than 3 amino acid substitutions from SEQ ID NO: 25 (Analog 24).

The spadin peptide, or any fragment thereof, may be present at any suitable amount within the composition. In some embodiments, the spadin peptide is present in the composition between about 0.25 wt % and 50 wt %, between 0.25 wt % and 75 wt %, or between 0.25 wt % and 90 wt %.

In some embodiments, the spadin peptide may be present at least about 0.25 wt %, at least about 0.5 wt %, at least about 1 wt %, at least about 2 wt %, at least about 3 wt %, at least about 5 wt %, at least about 8 wt %, at least about 10 wt %, at least about 20 wt %, at least about 30 wt %, at least about 40 wt %, at least about 50 wt %, at least about 60 wt %, at least about 70 wt %, at least about 80 wt %, or at least about 90 wt % of the entire composition can be the spadin peptide, or any fragment thereof. In some cases, the spadin peptide, or any fragment thereof, may be present at a concentration of no more than about 95 wt %, no more than about 90 wt %, no more than about 80 wt %, no more than about 70 wt %, no more than about 65 wt %, no more than about 60 wt %, no more than about 50 wt %, no more than about 40 wt %, no more than about 30 wt %, no more than about 20 wt %, or no more than about 10%. Combinations of any of these are also possible. For instance, the spadin peptide, or any fragment thereof, may be present at between about 8 wt % and about 65 wt %, or between about 0 wt % and about 10 wt %, etc.

In some embodiments, the compositions disclosed herein further comprise phenyl-N-tert-butylnitrone (PBN). PBN is an art recognized antioxidant and spin trap agent capable of reacting with and sequestering radical species that arise due to oxidative stress commonly associated with disease. In some embodiments, the PBN has the following structure:

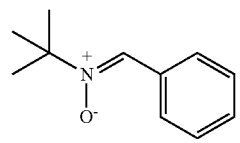

In other embodiments, the PBN is a functional derivative of the above structure. As recited above, PBN is capable of reacting with various radical species. Exemplary embodiments of said radical species includes, but is not limited to, reactive oxygen and nitrogen species such as hydroxyl radical, hydroxide ion, triplet oxygen, superoxide anion, peroxide ion, hydrogen peroxide, nitric oxide, peroxynitrite, among others.

The PBN, or any functional derivative thereof, may be present at any suitable amount within the compositions disclosed herein. In some embodiments, the PBN is present in the composition between about 0.25 wt % and 50 wt %, between 0.25 wt % and 75 wt %, or between 0.25 wt % and 90 wt %.

In some embodiments, the PBN is present in the composition at least about 0.25 wt %, at least about 0.5 wt %, at least about 1 wt %, at least about 2 wt %, at least about 3 wt %, at least about 5 wt %, at least about 8 wt %, at least about 10 wt %, at least about 20 wt %, at least about 30 wt %, at least about 40 wt %, at least about 50 wt %, at least about 60 wt %, at least about 70 wt %, at least about 80 wt %, or at least about 90 wt % of the entire composition can be the PBN, or any functional derivative thereof. In some cases, the PBN, or any functional derivative thereof, may be present at a concentration of no more than about 95 wt %, no more than about 90 wt %, no more than about 80 wt %, no more than about 70 wt %, no more than about 65 wt %, no more than about 60 wt %, no more than about 50 wt %, no more than about 40 wt %, no more than about 30 wt %, no more than about 20 wt %, or no more than about 10%. Combinations of any of these are also possible. For instance, the PBN, or any functional derivative thereof, may be present at between about 8 wt % and about 65 wt %, or between about 0 wt % and about 10 wt %, etc.

In some embodiments, the compositions disclosed herein further comprise benfotiamine. As used herein, the term "benfotiamine" is synonymous with S-benzoylthiamine O-monophosphate and Milgamma. Benfotiamine is an art recognized synthetic, fat-soluble, S-acyl derivative of thiamine (also known as vitamin B1). In some embodiments, the benfotiamine has the following structure:

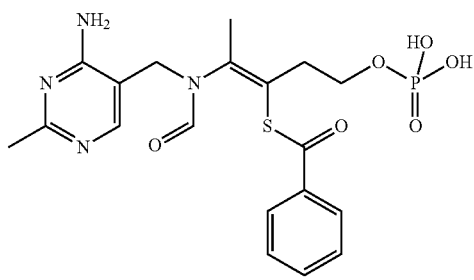 [SMILES: C/C(=C(\CCOP(=O)(O)O)SC(=O)c1ccccc1)N(C=O)Cc1cnc(C)nc1N]

In other embodiments, the benfotiamine is a functional derivative of the above structure.

Without wishing to be bound by any particular theory, it is believed that benfotiamine is capable of protecting nerves from damage (e.g., ototoxic drugs) and/or regenerating peripheral nerves, and hence, may improve hearing loss (e.g., in subjects diagnosed with hearing loss).

In some embodiments, benfotiamine may have synergistic effects with one or more components disclosed elsewhere herein (e.g., alpha-lipoic acid and/or dihexa). For example, in some embodiments, compositions comprising benfotiamine and alpha-lipoic acid prevent and/or restore hearing loss better than compositions comprising either benfotiamine or alpha-lipoic acid alone. In some embodiments, compositions comprising benfotiamine and dihexa prevent and/or restore hearing loss better than compositions comprising either benfotiamine or dihexa alone. In some embodiments, compositions comprising benfotiamine, alpha-lipoic acid, and dihexa prevent and/or restore hearing loss better than compositions comprising either benfotiamine, alpha-lipoic acid, or dihexa alone. In some embodiments, said improvements in hearing following application of said composition are synergistic (e.g., more than just additive).

The benfotiamine, or any functional derivative thereof, may be present at any suitable amount within the compositions disclosed herein. In some embodiments, the benfotiamine is present in the composition between about 0.1 wt % and 5 wt %, between 0.5 wt % and 4 wt %, or between 1 wt % and 3 wt %.

In some embodiments, the benfotiamine is present in the composition at least about 0.1 wt %, at least about 0.2 wt %, at least about 0.3 wt %, at least about 0.4 wt %, at least about 0.5 wt %, at least about 0.6 wt %, at least about 0.7 wt %, at least about 0.8 wt %, at least about 0.9 wt %, at least about 1.0 wt %, at least about 2 wt %, at least about 3 wt %, at least about 4 wt %, or at least about 5 wt % of the entire composition can be the PBN, or any functional derivative thereof. In some cases, the benfotiamine, or any functional derivative thereof, may be present at a concentration of no more than about 5 wt %, no more than about 4 wt %, no more than about 3 wt %, no more than about 2 wt %, no more than about 1.0 wt %, no more than about 0.9 wt %, no more than about 0.8 wt %, no more than about 0.7 wt %, no more than about 0.6 wt %, no more than about 0.5 wt %, no more than about 0.4 wt %, no more than 0.3 wt %, no more than 0.2 wt %, or no more than 0.1 wt %. Combinations of any of these are also possible. For instance, the benfotiamine, or any functional derivative thereof, may be present at between about 0.1 wt % and about 5 wt %, or between about 0.8 wt % and about 4 wt %, etc.

Without wishing to be bound by any particular theory, it is generally believed that the compositions disclosed herein may be delivered into the blood in certain embodiments to exert a therapeutic effect. Transdermal delivery may be used over injection (e.g., intravenous, percutaneous, subcutaneous, etc.) under certain conditions and embodiments. For example, transdermal delivery may provide a non-invasive alternative to parenteral routes, thus circumventing issues with needle phobia. The large surface area of skin and case of access allows many placement options, and transdermally delivered drugs have improved pharmacokinetic profiles, thus minimizing the risk of toxic side effects. There may also be other advantages as well, e.g., no first-pass effect by the liver. However, as discussed, the combination of dihexa and lipoic acid, spadin peptide, and/or PBN has not previously been applied transdermally.

The skin is the largest organ of the body, and its primary function is to provide a protective barrier between the body and the external environment against microorganisms, permeation of UV radiation, chemicals, allergens, and the loss of water. Again, without wishing to be bound by any particular theory, it is believed that transdermal delivery requires penetration of a drug, partitioning from the stratum corneum into the aqueous viable epidermis, diffusion through the viable epidermis into the upper dermis, permeation, and absorption into the systemic circulation, etc. This torturous pathway requires the drug to be low molecular weight (e.g., less than 500 Da), to have a balanced lipophilicity (e.g., log P=1-3), and to have a measurable solubility in both oil and in water. This is because the drug must first breach the lipophilic stratum corneum and then be resorbed into the aqueous central compartment of the systemic circulation. The log P of any compound may be predicted using online calculators, such as the web calculator provided by Molinspiration, or by using other techniques for predicting log P known to those of ordinary skill in the art. In some cases, the online calculators may require the artisan to convert the peptide sequence into a SMILE string for analysis. Peptide to SMILE conversion tools are also freely available to those of ordinary skill in the art, on-line or elsewhere (e.g., available from NovoPro or other websites).

The molecular weight of dihexa is greater than 500 Da and is predicted to have a log P value greater than 3 (e.g., dihexa has a predicted log P value of 3.29). Thus, it is surprising that dihexa, or any functional derivative thereof, can be successfully delivered transdermally, e.g., without the assistance of other drug delivery technologies. In some embodiments, topical compositions comprising dihexa and at least one other active ingredient (e.g., lipoic acid, spadin peptide, and/or PBN) may surprisingly be successfully delivered transdermally, especially if the at least one other active ingredient has a log P value of less than 1 or greater than 3 (e.g., spadin peptide 1-44 is predicted to have a log P value of about −5).

However, in some embodiments, dihexa, or a functional derivative thereof, in combination with one or more additional active ingredients, may be delivered transdermally. For example, as discussed herein, compounds such as lecithin, phosphatidylcholine, and/or other components that may facilitate delivery of dihexa, lipoic acid, spadin peptide, and/or PBN, through the skin. In addition, dihexa and spadin have a predicted log P values of greater than 3 and less than 1, respectively, suggesting that it may be difficult to deliver it transdermally, as it may not have balanced lipophilicity or measurable oil solubility.

In some embodiments, the compositions disclosed comprise a composition for delivery to the ear, comprising dihexa, or a functional derivative thereof, lipoic acid, or a functional derivative thereof, spadin peptide, or a functional derivative thereof, and PBN, or a functional derivative thereof. The ratio of dihexa:lipoic acid:spadin peptide:PBN may be any suitable ratio known to those of skill in the art. In some embodiments, the ratio of dihexa:lipoic acid:spadin peptide:PBN is any ratio that adds up to a value of 1 (if represented as fractions) or 100% (if represented as a percentage). For example, in some embodiments, the absolute ratio of dihexa:lipoic acid:spadin peptide:PBN may be any ratio listed in Table 1.

TABLE 1

Nonlimiting embodiments of possible ratios of active ingredients

| | Dihexa | Lipoic acid | Spadin Peptide | PBN |
|---|---|---|---|---|
| 1 | 0.25 | 0.25 | 0.25 | 0.25 |
| 2 | 0.25 | 0 | 0 | 0.75 |
| 3 | 0.25 | 0 | 0.75 | 0 |
| 4 | 0.25 | 0.75 | 0 | 0 |
| 5 | 0.75 | 0 | 0 | 0.25 |
| 6 | 0.75 | 0 | 0.25 | 0 |
| 7 | 0.75 | 0.25 | 0 | 0 |
| 8 | 0.5 | 0.25 | 0.25 | 0 |
| 9 | 0.5 | 0.25 | 0 | 0.25 |
| 10 | 0.5 | 0 | 0.25 | 0.25 |
| 11 | 0.8 | 0.05 | 0.05 | 0.1 |
| 12 | 0.8 | 0.1 | 0.05 | 0.05 |
| 13 | 0.8 | 0.05 | 0.1 | 0.05 |

In some embodiments, dihexa and the one or more active ingredients are present in the compositions at a relative ratio (e.g., relative to each other) of between 0.3:1 and 1:0.06. In some embodiments, the relative ratio of dihexa:lipoic acid is between 0.3:1 and 1:0.06. In some embodiments, the relative ratio is greater than or equal to 0.3:1, greater than or equal to 0.4:0.9, greater than or equal to 0.5:0.8, greater than or equal to 0.6:0.4, greater than or equal to 0.7:0.4, greater than or equal to 0.8:0.3, greater than or equal to 0.9:0.1, or greater than 1:0.06. In other embodiments, the relative ratio of dihexa:lipoic acid is less than or equal to 1:0.06, less than or equal to 0.9:0.1, less than or equal to 0.8:0.3, less than or equal to 0.7:0.4, less than or equal to 0.6:0.4, less than or equal to 0.5:0.8, less than or equal to 0.4:0.9, or less than or equal to 0.3:1. Other relative ratios are also possible in other embodiments.

In some embodiments, the relative ratio of dihexa:spadin peptide is between 0.3:1 and 1:0.06. In some embodiments, the relative ratio is greater than or equal to 0.3:1, greater than or equal to 0.4:0.9, greater than or equal to 0.5:0.8, greater than or equal to 0.6:0.4, greater than or equal to 0.7:0.4, greater than or equal to 0.8:0.3, greater than or equal to 0.9:0.1, or greater than 1:0.06. In other embodiments, the relative ratio of dihexa:spadin peptide is less than or equal to 1:0.06, less than or equal to 0.9:0.1, less than or equal to 0.8:0.3, less than or equal to 0.7:0.4, less than or equal to 0.6:0.4, less than or equal to 0.5:0.8, less than or equal to 0.4:0.9, or less than or equal to 0.3:1. Other relative ratios are also possible in other embodiments.

In some embodiments, the relative ratio of dihexa:PBN acid is between 0.3:1 and 1:0.06. In some embodiments, the relative ratio is greater than or equal to 0.3:1, greater than or equal to 0.4:0.9, greater than or equal to 0.5:0.8, greater than or equal to 0.6:0.4, greater than or equal to 0.7:0.4, greater than or equal to 0.8:0.3, greater than or equal to 0.9:0.1, or greater than 1:0.06. In other embodiments, the ratio of dihexa:PBN is less than or equal to 1:0.06, less than or equal to 0.9:0.1, less than or equal to 0.8:0.3, less than or equal to 0.7:0.4, less than or equal to 0.6:0.4, less than or equal to 0.5:0.8, less than or equal to 0.4:0.9, or less than or equal to 0.3:1. Other relative ratios are also possible in other embodiments.

In some embodiments, the relative ratio of lipoic acid:spadin peptide is between 0:1 and 1:0. In some embodiments, the relative ratio is greater than or equal to 0:1, greater than or equal to 0:2:0.8, greater than or equal to 0.3:0.7, greater than or equal to 0.4:0.6, greater than or equal to 0.5:0.5, greater than or equal to 0.6:0.4, greater than or equal to 0.7:0.3, greater than or equal to 0.8:0.2, greater than or equal to 0.9:0.1, or greater than or equal to 1:0. In some embodiments, the relative ratio is less than or equal to 1:0, less than or equal to 0.9:0.1, less than or equal to 0.8:0.2, less than or equal to 0.7:0.3, less than or equal to 0.6:0.4, less than or equal to 0.5:0.5, less than or equal to 0.4:0.6, less than or equal to 0.3:0.7, less than or equal to 0.2:0.8, less than or equal to 0.1:0.9, or less than or equal to 0:1. Other relative ratios are also possible in other embodiments.

In some embodiments, the relative ratio of lipoic acid:PBN is between 0:1 and 1:0. In some embodiments, the relative ratio is greater than or equal to 0:1, greater than or equal to 0:2:0.8, greater than or equal to 0.3:0.7, greater than or equal to 0.4:0.6, greater than or equal to 0.5:0.5, greater than or equal to 0.6:0.4, greater than or equal to 0.7:0.3, greater than or equal to 0.8:0.2, greater than or equal to 0.9:0.1, or greater than or equal to 1:0. In some embodiments, the relative ratio is less than or equal to 1:0, less than or equal to 0.9:0.1, less than or equal to 0.8:0.2, less than or equal to 0.7:0.3, less than or equal to 0.6:0.4, less than or equal to 0.5:0.5, less than or equal to 0.4:0.6, less than or equal to 0.3:0.7, less than or equal to 0.2:0.8, less than or equal to 0.1:0.9, or less than or equal to 0:1. Other relative ratios are also possible in other embodiments.

In some embodiments, the relative ratio of spadin peptide: PBN is between 0:1 and 1:0. In some embodiments, the relative ratio is greater than or equal to 0:1, greater than or equal to 0:2:0.8, greater than or equal to 0.3:0.7, greater than or equal to 0.4:0.6, greater than or equal to 0.5:0.5, greater than or equal to 0.6:0.4, greater than or equal to 0.7:0.3, greater than or equal to 0.8:0.2, greater than or equal to 0.9:0.1, or greater than or equal to 1:0. In some embodiments, the relative ratio is less than or equal to 1:0, less than or equal to 0.9:0.1, less than or equal to 0.8:0.2, less than or equal to 0.7:0.3, less than or equal to 0.6:0.4, less than or equal to 0.5:0.5, less than or equal to 0.4:0.6, less than or equal to 0.3:0.7, less than or equal to 0.2:0.8, less than or equal to 0.1:0.9, or less than or equal to 0:1. Other relative ratios are also possible in other embodiments.

In addition, in one set of embodiments, the spadin peptide, or any fragment thereof, may be delivered using one or more chemical enhancers, which may increase skin permeability. Any chemical enhancer known in the art may be used to enhance the permeation of the spadin peptide, or any fragments thereof, through the skin (e.g., to achieve therapeutic levels). Examples include, but are not limited to, 1-dodecylazacyloheptan-2-one (Azone) and 2-n-nonyl-1,3-dioxolane (SEPA). Any suitable amount of enhancer may be present within the composition. For example, at least about 0.25 wt %, at least about 0.5 wt %, at least about 1 wt %, at least about 2 wt %, at least about 3 wt %, at least about 5 wt %, at least about 8 wt %, at least about 10 wt %, at least about 20 wt %, at least about 30 wt %, at least about 40 wt %, at least about 50 wt %, at least about 60 wt %, at least about 70 wt %, at least about 80 wt %, or at least about 90 wt % of the entire composition can be enhancer. In some cases, the enhancer may be present at a concentration of no more than about 95 wt %, no more than about 90 wt %, no more than about 80 wt %, no more than about 70 wt %, no more than about 65 wt %, no more than about 60 wt %, no more than about 50 wt %, no more than about 40 wt %, no more than about 30 wt %, no more than about 20 wt %, or no more than about 10%. Combinations of any of these are also possible. For instance, the enhancer may be present at between about 8 wt % and about 65 wt %, or between about 0 wt % and about 10 wt %, etc.

As mentioned, in some aspects, components such as those described above may be present within a composition comprising a lecithin, such as phosphatidylcholine. The composition may be a cream or other formulations such as those described herein. In one set of embodiments, the composition may comprise liquid crystal multilamellar phosphatidylcholine. In some cases, the compositions are relatively free of oxygen ($O_2$) or water. Without wishing to be bound by any theory, it is believed that such compositions may serve to inhibit or reduce reaction of components within the composition from reacting with oxygen (e.g., in the air, or dissolved in water, etc.). Thus, in some cases, the compositions may be stable, and/or can be stored for periods of time with little or no loss or reaction of the components contained therein. In some cases, stability of the composition can be achieved at room temperature (about 25° C.), and/or at other storage temperatures such as those described herein.

In some embodiments, the composition is a composition for topical delivery comprising a topical formulation comprising dihexa, or any functional derivative thereof, lipoic acid, or any functional derivative thereof and lecithin. In certain embodiments, the topical composition further comprises spadin peptide, or a fragment thereof. In some embodiments, the spadin peptide, or any fragment thereof, comprises an amino acid sequence that is at least 85%, at least 90%, at least 95%, at least 99%, at least 99.5%, or at least 99.8% identical to the amino acid sequence of SEQ ID NO: 12 (Analog 11). In other embodiments, the topical composition further comprises PBN.

In some embodiments, the composition is a composition for topical delivery comprising a topical formulation comprising dihexa, or any functional derivative thereof, spadin peptide, or any fragment thereof and lecithin. In some embodiments, the spadin peptide, or any fragment thereof, comprises an amino acid sequence that is at least 85%, at least 90%, at least 95%, at least 99%, at least 99.5%, or at least 99.8% identical to the amino acid sequence of SEQ ID NO: 12 (Analog 11). In some embodiments, the topical formulation further comprises lipoic acid and/or PBN.

In some embodiments, the composition is a composition for topical delivery comprising a topical formulation comprising dihexa, or any functional derivative thereof, PBN, or any functional derivative thereof and lecithin. In some embodiments, the topical formulation further comprises a spadin peptide, or any fragment thereof, comprising an amino acid sequence that is at least 85%, at least 90%, at least 95%, at least 99%, at least 99.5%, or at least 99.8% identical to the amino acid sequence of SEQ ID NO: 12 (Analog 11). In some embodiments, the topical formulation further comprises lipoic acid, or a functional derivative thereof.

In one set of embodiments, the composition comprises a first phase comprising a lecithin such as phosphatidylcholine, which may be present within a second phase. The composition may also comprise an emulsifier, such as is discussed herein. Other components, for example, transdermal penetration enhancers, adjuvants, surfactants, lubricants, etc. can also be present in certain cases.

The compositions comprise, in certain embodiments, a phase comprising phosphatidylcholine and/or other lecithin's in which the components may be contained within, e.g., to reduce the ability of oxygen (e.g., from the air) to react with such components. In some cases, the phosphatidylcholine or lecithin may be contained within a second phase. In some cases, the composition may have phosphatidylcholine or lecithin in the form of vesicles, e.g., micelles or liposomes. The phosphatidylcholine or lecithin composition can be unilamellar or multilamellar in some embodiments. However, in some instances, the phosphatidylcholine or lecithin may be present as a liquid crystal arrangement, rather than a vesicular or liposomal arrangement.

In some cases, certain components may be contained within water or other aqueous environment within the composition (e.g., within vesicles such as liposomes or an emulsion or a liquid crystal structure within the composition, etc.), although in some embodiments, little or no water is used, and some or all of the components are directly contained within the phosphatidylcholine or other lecithin within the composition.

In certain embodiments, the composition, or at least a phase of the composition (e.g., containing pyruvic acid and/or pyruvate and/or antioxidants) is substantially free of water, e.g., comprising no more than about 10 wt %, no more than about 3 wt %, no more than about 1 wt %, no more than about 0.3 wt %, or no more than about 0.1 wt % water (i.e., relative to the weight of the overall composition). The composition may also have no more than about 1,000 ppm, no more than about 750 ppm, no more than about 500 ppm, no more than about 400 ppm, no more than about 300 ppm, no more than about 250 ppm, no more than about 200 ppm, no more than about 150 ppm, no more than about 100 ppm, no more than about 50 ppm, no more than about 25 ppm, or no more than about 10 ppm of water (by weight). In certain embodiments, no detectable water may be present in the composition, or at least within one phase of the composition. Any suitable technique can be used for determining the amount of water present in the composition, for example, Karl-Fisher titration. In some cases, the composition may also be free of any liquids that typically contain water, e.g., physiological buffers, bodily fluids, saline, blood, or the like.

In addition, in some embodiments, the composition is substantially free of gaseous oxygen ($O_2$). For instance, the composition may also have no more than about 1,000 ppm, no more than about 750 ppm, no more than about 500 ppm, no more than about 400 ppm, no more than about 300 ppm, no more than about 250 ppm, no more than about 200 ppm, no more than about 150 ppm, no more than about 100 ppm, no more than about 50 ppm, no more than about 25 ppm, or no more than about 10 ppm of oxygen (by weight).

Phosphatidylcholine (herein abbreviated "PC") is a basic component of cell membrane bilayers and the main phospholipid circulating in the plasma of blood. Phosphatidylcholine typically has a phospholipid structure with a choline head group and a glycerophosphoric acid tail group. The tail group can be saturated or unsaturated. More than one tail group may be present in the phosphatidylcholine in some cases, and the tail groups may be the same or different. Specific non-limiting examples of phosphatidylcholines that could be used include one or a mixture of stearic, palmitic, margaric, and/or oleic acid diglycerides linked to a choline ester head group.

Phosphatidylcholines are a member of a class of compounds called lecithins. Typically, a lecithin is a composed of phosphoric acid, choline, fatty acids, glycerol, glycolipids, triglycerides, and/or phospholipids. In some cases, other lecithins may be used, in addition to or instead of a phosphatidylcholine. Non-limiting examples of other lecithins include phosphatidylethanolamine, phosphatidylinositol, or phosphatidic acid. Many commercial lecithin products are available, such as, for example, Lecithol®, Vitellin®, Kelecin®, and Granulestin®. Lecithin is widely used in the food industry. In some embodiments, certain compositions can contain synthetic or natural lecithin, or mixtures thereof. Natural preparations are used in some cases because they exhibit desirable physical characteristics, and/or may be economical or nontoxic. However, in other embodiments, non-natural preparations are used, or the composition can include both natural and non-natural preparations.

Any suitable amount of phosphatidylcholine or lecithin may be present within the composition. For example, at least about 0.25 wt %, at least about 0.5 wt %, at least about 1 wt %, at least about 2 wt %, at least about 3 wt %, at least about 5 wt %, at least about 8 wt %, at least about 10 wt %, at least about 20 wt %, at least about 30 wt %, at least about 40 wt %, at least about 50 wt %, at least about 60 wt %, at least about 70 wt %, at least about 80 wt %, or at least about 90 wt % of the entire composition can be a phosphatidylcholine or a lecithin. In some cases, the phosphatidylcholine or lecithin may be present at a concentration of no more than about 95 wt %, no more than about 90 wt %, no more than about 80 wt %, no more than about 70 wt %, no more than about 65 wt %, no more than about 60 wt %, no more than about 50 wt %, no more than about 40 wt %, no more than about 30 wt %, no more than about 20 wt %, or no more than about 10%. Combinations of any of these are also possible. For instance, the phosphatidylcholine or lecithin may be present at between about 8 wt % and about 65 wt %, or between about 0 wt % and about 10 wt %, etc. One or more than one type of phosphatidylcholine or lecithin may be present.

In some embodiments, the composition comprises a phosphatidylcholine, e.g., any of those described herein. The composition can include any suitable amount of phosphatidylcholine, for example, at least about 1 wt %, at least about 3 wt %, at least about 5 wt %, at least about 10 wt %, at least about 20 wt %, at least about 30 wt %, at least about 40 wt %, at least about 50 wt %, at least about 60 wt %, at least about 70 wt %, at least about 80 wt %, at least about 90 wt % etc. In some cases, no more than about 90 wt %, no more than about 80 wt %, no more than about 70 wt %, no more than about 60 wt %, no more than about 50 wt %, no more than about 40 wt %, no more than about 30 wt %, no more than about 20 wt %, no more than about 10 wt %, or no more than about 5 wt % of the composition is phosphatidylcholine. Combinations of any of these are also possible. For example, the composition may be between about 0 wt % and about 10 wt % phosphatidylcholine. The composition may include one or more than one phosphatidylcholine. One non-limiting example of a phosphatidylcholine is Phospholipon-90G (American Lecithin Company).

Some compositions may contain polyenylphosphatidylcholine (herein abbreviated "PPC"). In some cases, PPC can be used to enhance epidermal penetration. The term "polyenylphosphatidylcholine," as used herein, means any phosphatidylcholine bearing two fatty acid moieties, wherein at least one of the two fatty acids is an unsaturated fatty acid with at least two double bonds in its structure, such as linoleic acid.

Certain types of soybean lecithin and soybean fractions, for example, can contain higher levels of polyenylphosphatidylcholine, with dilinoleoylphosphatidylcholine (18:2-18:2 phosphatidylcholine) as the most abundant phosphatidylcholine species therein, than conventional food grade lecithin. Such lecithins may be useful in formulating certain delivery compositions. In some embodiments, conventional soybean lecithin may be enriched with polyenylphosphatidylcholine, for instance, by adding soybean extracts containing high levels of polyenylphosphatidylcholine. As used herein, this type of phosphatidylcholine is called "polyenylphosphatidylcholine-enriched" phosphatidylcholine (hereinafter referred to as PPC-enriched phosphatidylcholine), even where the term encompasses lecithin obtained from natural sources exhibiting polyenylphosphatidylcholine levels higher than ordinary soybean varieties. These products are commercially available, for example, from American Lecithin Company, Rhone-Poulenc and other lecithin vendors. American Lecithin Company markets its products with a "U" designation, indicating high levels of unsaturation; Rhone-Poulenc's product is a soybean extract containing about 42% dilinoleoylphosphatidylcholine and about 24% palmitoyllinoleylphosphatidylcholine (16:0 to 18:2 of PC) as the major phosphatidylcholine components. Another example of a suitable polyenylphosphatidylcholine is NAT 8729 (also commercially available from vendors such as Rhone-Poulenc and American Lecithin Company).

In some embodiments, various compositions are formulated to be substantially clear or substantially transparent. Transparency may be useful, for instance, for product acceptance in the marketplace, e.g., when applied to the skin of a subject. However, in other embodiments, the composition is not necessarily transparent. Certain substances can be useful in providing a substantially transparent composition, for example, fatty acid esters such as ascorbate palmitate or isopropyl palmitate. In one set of embodiments, the composition may be substantially transparent such that incident visible light (e.g., have wavelengths of between about 400 nm and about 700 nm) can be transmitted through 1 cm of the composition with a loss in intensity of no more than about 50%, about 60%, about 70%, about 80%, or about 90% relative to the incident light. In some embodiments, there may be no substantial difference in the wavelengths that are absorbed by the composition (i.e., white light passing through the composition appears white), although in other cases, there can be more absorption at various wavelengths (for example, such that white light passing through the composition may appear colored).

Other components may also be present within the composition, in accordance with certain embodiments. For example, the composition may include volatile organic fluids, fatty acids, volatile aromatic cyclic compounds, high molecular weight hydrocarbons, or the like.

Any suitable amount of polyenylphosphatidylcholine or lecithin may be present within the composition. For example, at least about 0.25 wt %, at least about 0.5 wt %, at least about 1 wt %, at least about 2 wt %, at least about 3 wt %, at least about 5 wt %, at least about 8 wt %, at least about 10 wt %, at least about 20 wt %, at least about 30 wt %, at least about 40 wt %, at least about 50 wt %, at least about 60 wt %, at least about 70 wt %, at least about 80 wt %, or at least about 90 wt % of the composition can be polyenylphosphatidylcholine or lecithin. In some cases, the polyenylphosphatidylcholine or lecithin may be present at a concentration of no more than about 95 wt %, no more than about 90 wt %, no more than about 80 wt %, no more than about 70 wt %, no more than about 65 wt %, no more than about 60 wt %, no more than about 50 wt %, no more than about 40 wt %, no more than about 30 wt %, no more than about 20 wt %, or no more than about 10%. Combinations of any of these are also possible. For instance, the polyenylphosphatidylcholine or lecithin may be present at between about 8 wt % and about 65 wt %. In some embodiments, at least about 20 wt %, at least about 30 wt %, at least about 40 wt %, at least about 50 wt %, at least about 60 wt %, at least about 70 wt %, at least about 80 wt %, at least about 90 wt %, or about 100 wt % of all of the phosphatidylcholine or lecithin in the composition is polyenylphosphatidylcholine.

While not wishing to be bound to any theory, it is believed that the PPC-enriched phosphatidylcholine may contribute to the stability of the composition, and/or by enhancing its penetration into the skin or other area, e.g., a mucosal surface.

In certain embodiments, a composition such as those described herein can be formulated to include a first phase and a second phase. Typically, the second phase is substantially immiscible with the first phase comprising phosphatidylcholine or lecithin. Two phases that are substantially immiscible are able to form discrete phases when exposed to each other at ambient conditions (e.g., 25° C. and 1 atm) for extended periods of time (e.g., at least about a day). The phases can be separate identifiable phases (e.g., one may float above the other), or in some cases, the phases are intermingled, e.g., as in an emulsion. The stability of the discrete phases may be kinetic and/or thermodynamic in nature, in various embodiments.

In one set of embodiments, an emulsifier may be present, and in some cases, the emulsifier may cause the first phase comprising phosphatidylcholine or lecithin to form a liquid crystal, and/or vesicles such as micelles or liposomes. In some cases, multilamellar structures may be present within the liquid crystal phase, although in other cases, only unilamellar structures may be present. For example, in certain cases, the PPC-enriched phosphatidylcholine can be loosely arranged in a multilamellar fashion. In some cases, the first phase (e.g., comprising PPC-enriched phosphatidylcholine) and the second phase can form a structure such as is disclosed in U.S. Pat. No. 7,182,956 to Perricone, et al. This is believed (without wishing to be bound by any theory) to form a loosely arranged, yet stable, PPC-enriched phosphatidylcholine-drug complex that may allow penetration and delivery of components and optional adjunct ingredients to the skin.

The emulsifier, in one embodiment, may be a substance that is able to stabilize an emulsion by increasing its kinetic stability. The emulsifier may also be chosen in some cases to be relatively inert or non-toxic relative to the skin or to a mucosal surface.

A variety of emulsifiers can be used, and many emulsifiers are readily available commercially. In one embodiment, for example, the emulsifier comprises a surfactant. Non-limiting examples of surfactants include a siloxylated polyether comprising dimethyl, methyl(propylpolyethylene oxide propylene oxide, acetate) siloxane commercially available from vendors such as Dow Corning (Dow Corning 190 surfactant). Other examples of materials that can be used as (or within) the second phase (e.g., as emulsifiers) include, but are not limited to, 1,2-propanediol, or silicone fluids containing low viscosity polydimethylsiloxane polymers, methylparaben (p-hydroxy benzoic acid methyl ester) commercially available from vendors such as Dow Corning (Dow Corning 200 silicone fluid). Still other examples include various siloxane or silicone compounds, e.g., hexamethyldisiloxane, amodimethicone, phenyltrimethicone, etc.

As yet another example, the surfactant may be a non-ionic surfactant. Examples include, but are not limited to polysorbates such as Polysorbate 20 (polyoxyethylene (20) sorbitan monolaurate), Polysorbate 40 (polyoxyethylene (20) sorbitan monopalmitate),Polysorbate 60 (polyoxyethylene (20) sorbitan monostearate), or Polysorbate 80 (polyoxyethylene (20) sorbitan monooleate), or sorbitan esters such as sorbitan monolaurate, sorbitan monopalmitate, sorbitan monostearate, sorbitan monooleate, sorbitan sesquioleate, sorbitan trioleate, or sorbitan isostearate.

In some embodiments, the second phase may comprise a polyglycol. The polyglycol may include a polyhydric alcohol of a monomeric glycol such as polyethylene glycol (PEG) and/or polypropylene glycol (PPG). For example, the PEG or PPG may be PEG or PPG 200, 300, 400, 600, 1,000, 1,450, 3,350, 4,000, 6,000, 8,000, and 20,000, where the number indicates the approximate average molecular weight of the PEG or PPG. As is understood by those of ordinary skill in the art, a polyglycol composition often will comprise a range of molecular weights, although the approximate average molecular weight is used to identify the type polyglycol. More than one PEG and/or PPG can also be present in certain instances.

More than one PEG and/or PPG can also be present in certain instances. The composition can include any suitable amount of polyglycol, for example, at least about 1 wt %, at least about 3 wt %, at least about 5 wt %, at least about 10 wt %, at least about 20 wt %, at least about 30 wt %, at least about 40 wt %, at least about 50 wt %, etc. In some cases, no more than about 60 wt %, no more than about 50 wt %, no more than about 40 wt %, no more than about 30 wt %, no more than about 20 wt %, no more than about 18 wt %, no more than about 15 wt %, no more than about 12 wt %, or no more than about 10 wt % of the composition is polyglycol. Combinations of any of these are also possible. For example, the composition may be between about 0 wt % and about 10 wt % polyglycol. The composition may include one or more than one type of polyglycol.

Additionally, purified water may be present in the second phase in some embodiments, although in other cases, little or no water is present in the second phase. For example, the first phase, the second phase, can contain less than 10%, less than 5%, less than 2%, less than 1%, or less that 0.05% (e.g., wt %) of water relative to the weight of the respective phase or of the entire composition. In some cases, the second phase may also comprise adjunct ingredients such as those described herein.

The second phase may include any one, or more than one, of the materials described above. In addition, any suitable amount of second phase can be used in accordance with various embodiments. For example, the second phase may be present at least about 10 wt %, at least about 20 wt %, at least about 30 wt %, at least about 40 wt %, at least about 50 wt %, at least about 60 wt %, at least about 70 wt %, at least about 80 wt %, or at least about 90 wt % of the composition. In some cases, the ratio of the first phase (e.g., comprising phosphatidylcholine or lecithin) to the second phase can be at least about 1:3, at least about 1:2, at least about 1:1, at least about 2:1, at least about 3:1, or at least about 4:1, etc.

As a specific non-limiting example of one set of embodiments, a polyenylphosphatidylcholine comprises a certain material with the trade name NAT 8729, and optionally at least one polyglycol (e.g., PEG or PPG, such as is described herein). The composition can also comprise a PPC-enriched phosphatidylcholine material that is present within the first or second phase, e.g., comprising various components such as pyruvic acid, pyruvate, antioxidants such as those described herein, etc. The second phase may also comprise a surfactant such as a siloxylated polyether comprising dimethyl, methyl(propylpolyethylene oxide propylene oxide, acetate) siloxane commercially available from vendors such as Dow Corning (Dow Corning 190 surfactant) and lubricant such as silicone fluids containing low viscosity polydimethylsiloxane polymers, methylparaben (p-hydroxy benzoic acid methyl ester) commercially available from vendors such as Dow Corning (Dow Corning 200 silicone fluid).

Other examples of materials that can be used as (or within) the formulation include, but are not limited to, benzyl alcohol, ethyl alcohol, isopropyl palmitate (IPP), propanediol, and caprylic/capric triglycerides.

As another example, the first phase also comprises, in some embodiments, a fatty acid ester. Non-limiting examples include ascorbate palmitate or isopropyl palmitate. In some cases, the fatty acid ester is used as a preservative or an antioxidant. The composition can include any suitable amount of fatty acid ester, for example, at least about 1 wt %, at least about 3 wt %, at least about 5 wt %, at least about 10 wt %, at least about 20 wt %, at least about 30 wt %, at least about 40 wt %, at least about 50 wt %, etc. In some cases, no more than about 60 wt %, no more than about 50 wt %, no more than about 40 wt %, no more than about 30 wt %, no more than about 20 wt %, no more than about 18 wt %, no more than about 15 wt %, no more than about 12 wt %, or no more than about 10 wt % of the composition is fatty acid ester. Combinations of any of these are also possible. For example, the composition may be between about 0 wt % and about 10 wt % fatty acid ester. The composition may include one or more than one fatty acid ester.

In another set of embodiments, the composition may also include one or more transdermal penetration enhancers. Examples of transdermal penetration enhancers include, but are not limited to, 1,3-dimethyl-2-imidazolidinone or 1,2-propanediol. Other examples include cationic, anionic, or nonionic surfactants (e.g., sodium dodecyl sulfate, polyoxamers, etc.); fatty acids and alcohols (e.g., ethanol, oleic acid, lauric acid, liposomes, etc.); anticholinergic agents (e.g., benzilonium bromide, oxyphenonium bromide); alkanones (e.g., n-heptane); amides (e.g., urea, N,N-dimethyl-m-toluamide); organic acids (e.g., citric acid); sulfoxides (e.g., dimethylsulfoxide); terpenes (e.g., cyclohexene); ureas; sugars; carbohydrates or other agents. The transdermal penetration enhancers can be present in any suitable amount within the composition. For example, at least about 10 wt %, at least about 20 wt %, at least about 30 wt %, at least about 40 wt %, or at least about 50 wt % of the composition may comprise one or more transdermal penetration enhancers. In some cases, no more than about 60 wt %, no more than about 50 wt %, no more than about 40 wt %, no more than about 30 wt %, no more than about 20 wt %, no more than about 10 wt %, no more than about 9 wt %, or no more than about 5 wt % of the composition comprises transdermal penetration enhancers. Combinations of any of these are also possible. For example, the composition may have between about 0 wt % and about 5 wt % of one or more transdermal penetration enhancers.

In other embodiments, the composition may be modified in order to control depth of penetration. For example, in certain embodiments, the composition includes one or more polymers that act to reduce penetration depth of various components, etc. Controlled depth of penetration may be important for indications where local administration is desired without systemic effects. Examples of transdermal penetration barrier polymers include, but are not limited to, silicone waxes, acrylate polymers, and dimethicone copolymers. In certain embodiments, a transdermal penetration barrier polymer is nonionic. A transdermal penetration barrier polymer can be present in any suitable amount within the composition. For example, at least about 10 wt %, at least about 20 wt %, at least about 30 wt %, at least about 40 wt %, or at least about 50 wt % of the composition may comprise one or more transdermal penetration barrier polymers. In some cases, no more than about 60 wt %, no more than about 50 wt %, no more than about 40 wt %, no more than about 30 wt %, no more than about 20 wt %, no more than about 10 wt %, no more than about 9 wt %, or no more than about 5 wt % of the composition comprises a transdermal penetration barrier polymer. Combinations of any of these are also possible. For example, the composition may have between about 0 wt % and about 5 wt % of one or more transdermal penetration barrier polymers.

In some embodiments, various compositions are formulated to be substantially clear or substantially transparent. Transparency may be useful, for instance, for product acceptance in the marketplace, e.g., when applied to the skin of a subject. However, in other embodiments, the composition is not necessarily transparent. Certain substances can be useful in providing a substantially transparent composition, for example, fatty acid esters such as ascorbate palmitate or isopropyl palmitate. In one set of embodiments, the composition may be substantially transparent such that incident visible light (e.g., have wavelengths of between about 400 nm and about 700 nm) can be transmitted through 1 cm of the composition with a loss in intensity of no more than about 50%, about 60%, about 70%, about 80%, or about 90% relative to the incident light. In some embodiments, there may be no substantial difference in the wavelengths that are absorbed by the composition (i.e., white light passing through the composition appears white), although in other cases, there can be more absorption at various wavelengths (for example, such that white light passing through the composition may appear colored).

Other components may also be present within the composition, in accordance with certain embodiments. For example, the composition may include volatile organic fluids, fatty acids, volatile aromatic cyclic compounds, high molecular weight hydrocarbons, or the like.

As mentioned, in some embodiments, the components may be stable at room temperature. In some cases, the components may be released, for example, when the composition is exposed to an aqueous environment, e.g., within the body. Without wishing to be bound by any theory, it is believed that when the composition is applied to the skin, the liquid crystal structure collapses, delivering components to the skin or other desired area of treatment. The concentration of the components inside the liquid crystal matrix can be varied in terms of concentration. The matrix also may act as a sustained release delivery system in some embodiments. It is also believed that the liquid crystal is highly penetrating, such that the components can be delivered to the epidermis, dermis and dermal vascular for systemic release as well as to subcutaneous fat, at least under some conditions.

Thus, a composition such as is discussed herein may be prepared and/or stored at any suitable temperature and under any suitable conditions. In some embodiments, for instance, a composition can be prepared and/or stored under limited or no oxygen conditions. The composition can also be prepared and/or stored under limited or no nitrogen and/or carbon dioxide. For instance, the composition may be prepared and/or stored in a sealed environment (e.g., stored in a sealed container). The sealed environment (e.g., container) can be at least substantially devoid of gas, and/or contains a gaseous mixture that excludes, or at least is depleted in, oxygen. In some embodiments, an environment depleted in oxygen may have less than about 20%, less than about 15%, less than about 10%, less than about 5%, about 1% or less, about 0.1% or less, about 0.01% or less, about 0.001% or less, oxygen (e.g., as a wt % or as molar % per volume). For example, the gaseous mixture may include a noble gas, such as argon, helium, neon, etc. In one set of embodiments, the container may comprise a multi-layered metallic and/or polymeric barrier, e.g., formed from Glaminate® (American Can Company). For instance, the container may have the shape of a tube. Thus, in certain embodiments, the container is substantially resistant to oxygen permeation, nitrogen permeation, and/or carbon dioxide permeation. In certain embodiments, the container is substantially watertight, for example, such that substantially no water is absorbed by the container, or such that no water is able to pass through the container even if the container is filled with water.

In certain embodiments, the composition may be stored at temperatures of less than about 80° C., less than about 70° C., less than about 60° C., less than about 50° C., less than about 40° C., less than about 30° C., less than about 25° C., less than about 20° C., less than about 15° C., less than about 10° C., less than about 5° C., less than about 0° C., etc., for extended periods of time, e.g., at least about a day, at least about a week, at least about 4 weeks, at least about 2 months, at least about 3 months, at least about 4 months, at least about 6 months, at least about 1 year, at least about 2 years, at least about 3 years, etc.

In accordance with certain embodiments, a composition as discussed herein may be prepared by mixing at least a first phase and a second phase together. More than two phases may be combined in some cases. The second phase can comprise an emulsifier, or any other components discussed herein. The first phase may comprise a lecithin such as phosphatidylcholine and/or polyenylphosphatidylcholine, e.g., PPC-enriched phosphatidylcholine, for instance, as described herein. In some embodiments, other components are also mixed into the composition, for example, transdermal penetration enhancers, adjuvants, polyglycols (e.g., PEG and/or PPG), surfactants, lubricants, etc. as discussed herein.

In some embodiments, a composition may be prepared as discussed above, then diluted, e.g., with a diluent, to produce a final composition. For example, a "stock" composition may be initially prepared, then the stock composition diluted to produce a final composition, e.g., before use, before storage, before packaging, etc. In some embodiments, the diluent used may be a component as discussed herein (for example, forming at least a portion of the second phase), and the same or different materials than may be present in the initial composition may be used. The dilution ratio (amount of diluent added, relative to the initial composition) may be at least about 2, at least about 3, at least about 5, at least about 10, at least about 15, at least about 20, at least about 25, at least about 30, at least about 50, or at least about 100, or any other suitable factor.

A composition may be prepared and/or stored at any suitable temperature and under any suitable conditions. In some embodiments, for instance, a composition can be prepared and/or stored under limited or no oxygen conditions. The composition can also be prepared and/or stored under limited or no nitrogen and/or carbon dioxide. For instance, the composition may be prepared and/or stored in a sealed environment (e.g., stored in a sealed container). The sealed environment (e.g., container) can be at least substantially devoid of gas, and/or contains a gaseous mixture that excludes, or at least is depleted in, oxygen. In some embodiments, an environment depleted in oxygen may have less than about 20%, less than about 15%, less than about 10%, less than about 5%, about 1% or less, about 0.1% or less, about 0.01% or less, about 0.001% or less, oxygen (e.g., as a wt % or as molar % per volume). For example, the gaseous mixture may include a noble gas, such as argon, helium, neon, etc. In one set of embodiments, the container may comprise a multi-layered metallic and/or polymeric barrier, e.g., formed from Glaminate® (American Can Company). For instance, the container may have the shape of a tube. Thus, in certain embodiments, the container is substantially resistant to oxygen permeation, nitrogen permeation, and/or carbon dioxide permeation. In certain embodiments, the container is substantially watertight, for example, such that substantially no water is absorbed by the container, or such that no water is able to pass through the container even if the container is filled with water. In some cases, the composition may be prepared and/or stored under relatively low relative humidities (RH) (e.g., less than about 50% RH, less than about 40% RH, less than about 30% RH, less than about 20% RH, or less than about 10% RH), and/or in the presence of a suitable desiccant, such as phosphorous pentoxide or silica gel.

In certain aspects, a composition such as those described herein may be applied to the skin, e.g., for topical or transdermal delivery. In some cases, the composition is a cream, although other formulations are also possible in some instances, e.g., a liquid, a gel, a cream, a lotion, an ointment, a soap, a solid "stick," or the like, such as is discussed herein.

In some cases, the composition may a viscosity of at least about 1,000 cP, at least about 2,000 cP, at least about 3,000 cP, at least about 5,000 cP, at least about 7,000 cP, at least about 10,000 cP, at least about 12,000 cP, at least about 15,000 cP, at least about 20,000 cP, at least about 30,000 cP, at least about 40,000 cP, at least about 50,000 cP, at least about 60,000 cP, at least about 70,000 cP, or at least about 80,000 cP.

For example, in some embodiments, application of compositions such as those described herein may be applied to the skin of a subject, e.g., to increase fat deposits within the skin, and/or to rejuvenate the appearance of the skin. Additionally, in some embodiments, the composition may be applied in conjunction with other types of treatments to a subject, e.g., to the skin of a subject, for treatment of any of the diseases, conditions, or needs described herein. These may be occur, e.g., simultaneously or sequentially, in various embodiments. Thus, certain compositions as described herein may be used to treat a wide variety of diseases or conditions. To "treat" a disorder, as used herein, means to reduce or eliminate a sign or symptom of the disorder, to stabilize the disorder, to inhibit the disorder, and/or to reduce or slow further progression of the disorder. The subject may be a human subject, or a non-human mammal in some cases.

In certain cases, a composition such as those described herein can be administered to a subject, such as a human subject, by rubbing it on the skin, e.g., in areas located at or at least within the vicinity of a desired target area. Other areas have also been described herein, in other embodiments. Without wishing to be bound by any theory, it is believed that phosphatidylcholine provides or facilitates delivery of the compounds described herein to the skin, allowing the components to be delivered to a target area. In some embodiments, the composition can be applied by rubbing the composition against the skin, or to the mucosal surface, which allows the composition (or at least, the compounds described herein and/or related compounds) to be absorbed by the skin.

The composition can be applied once, or more than once. For example, the composition may be administered at predetermined intervals. In some embodiments, for instance, the composition may be applied once per day, twice per day, 3 times per day, 4 times per day, once every other day, once every three days, once every four days, etc. The amount or concentration of the compounds necessary to bring about the therapeutic treatment is not fixed per se, and may depend upon factors such as the desired outcome, the type and severity the disease or condition, the concentration of the compounds present within the composition, etc.

Thus, some embodiments provide methods of administering the compositions disclosed herein to a subject. When administered, the compositions are applied in a therapeutically effective, pharmaceutically acceptable amount as a pharmaceutically acceptable formulation. Any of the compositions may be administered to the subject in a therapeutically effective dose. When administered to a subject, effective amounts will depend on the particular condition being treated and the desired outcome. A therapeutically effective dose may be determined by those of ordinary skill in the art, for instance, employing factors such as those described herein and using no more than routine experimentation.

For instance, in some embodiments the method comprises applying, to the skin behind the outer car of a subject, a topical composition comprising dihexa, or a functional derivative thereof, lipoic acid, or a functional derivative thereof, spadin peptide, or any fragment thereof, and PBN, or a functional derivative thereof. In some embodiments, the compositions further comprises a lecithin (e.g., phosphatidylcholine). In some embodiments, the method comprises applying a topical composition comprising dihexa, or a functional derivative thereof, lipoic acid, or a functional derivative thereof, spadin peptide, or any fragment thereof, and PBN, or a functional derivative thereof, to the eardrum of a subject in need thereof.

The methods described herein may be useful for treating hearing loss in a subject (e.g., conductive hearing loss, sensorineural hearing loss, and mixed hearing loss). In one set of embodiments, the methods are useful for treating sensorineural hearing loss in a subject. Accordingly, in some embodiments, the method is a method for treating hearing loss in a subject comprising administering a therapeutic amount of a composition comprising (i) dihexa, or a functional derivative thereof, and (ii) alpha-lipoic acid, or a functional derivative thereof, to the car of a subject, wherein the alpha-lipoic acid enhances the therapeutic effect of the dihexa. Without wishing to be bound by any particular theory, it is believed that increasing production of neural growth factor (NGF) via administration of lipoic acid will act synergistically with dihexa, or any functional derivative thereof, to promote survival and/or regeneration of hair cells of the middle car. In some embodiments, the composition is administered on the skin behind the outer car. In other embodiments, the composition is administered to the eardrum.

In some embodiments, the method is a method for treating hearing loss in a subject comprising administering a therapeutic amount of a composition comprising (i) dihexa, or any functional derivative thereof, and (ii) a spadin peptide or a retroinverso analog of a spadin peptide, or any fragment thereof, to the car of the subject in need. In some embodiments, the spadin peptide enhances the therapeutic effect of the dihexa. In other embodiments, the retroinverso analog of a spadin peptide enhances the therapeutic effect of dihexa. In some embodiments, the composition is administered on the skin behind the outer car. In other embodiments, the composition is administered to the eardrum.

In some embodiments, the method is a method for treating hearing loss in a subject comprising administering a therapeutic amount of a composition comprising (i) dihexa, or any functional derivative thereof, and (ii) a PBN, or any functional derivative thereof, to the car of the subject in need. In some embodiments, the PBN enhances the therapeutic effect of the dihexa. In some embodiments, the composition is administered on the skin behind the outer car. In other embodiments, the composition is administered to the eardrum.

In some embodiments, the method is a method for treating hearing loss in a subject comprising administering a therapeutic amount of a composition comprising (i) dihexa, or any functional derivative thereof, (ii) lipoid acid, or a functional derivative thereof, (iii) a spadin peptide or any fragment thereof, and/or (iv) a PBN, or any functional derivative thereof, to the car of the subject in need. In some embodiments, the combination of lipoic acid, spadin peptide, and PBN enhances the therapeutic effect of the dihexa. In some embodiments, the composition is administered on the skin behind the outer car. In other embodiments, the composition is administered to the eardrum.

In certain embodiments, the administration of various compositions may be designed so as to result in sequential exposures to the composition over a certain time period, for example, hours, days, weeks, months, or years. This may be accomplished, for example, by repeated administrations of a composition by one or more of the methods described herein, or by a sustained or controlled release delivery system in which the composition is delivered over a prolonged period without repeated administrations. Administration of the composition using such a delivery system may be, for example, by a transdermal patch. Maintaining a substantially constant concentration of the composition may be preferred in some cases.

For certain chronic treatments or therapies, it is contemplated that a composition as discussed herein may be used to deliver the compounds described herein to the skin or mucosal surface at a relatively high concentration during an initial treatment, and the amount of may be lowered or "titrated" down to a relatively lower concentration maintenance dose or amount.

In one set of embodiments, compositions described herein can be administered to a subject in a dosage range from between about 0.01 to about 10,000 mg/kg body weight/day, about 0.01 to about 5000 mg/kg body weight/day, about 0.01 to about 3000 mg/kg body weight/day, about 0.01 to about 1000 mg/kg body weight/day, about 0.01 to about 500 mg/kg body weight/day, about 0.01 to about 300 mg/kg body weight/day, about 0.01 to about 100 mg/kg body weight/day.

In one set of embodiments, the dosage may be between about 0.01 mg and about 500 g, between about 0.01 mg and about 300 g, between about 0.01 mg and about 100 g, between about 0.01 mg and about 30 g, between about 0.01 mg and about 10 g, between about 0.01 mg and about 3 g, between about 0.01 mg and about 1 g, between about 0.01 mg and about 300 mg, between about 0.01 mg and about 100 mg, between about 0.01 mg and about 30 mg, between about 0.01 mg and about 10 mg, between about 0.01 mg and about 3 mg, between about 0.01 mg and about 1 mg, between about 0.01 mg and about 0.3 mg, or between about 0.01 mg and about 0.1 mg.

In another set of embodiments, the dosage may be at least about 0.01 mg, at least about 0.02 mg, at least about 0.03 mg, at least about mg, at least about 0.05 mg, at least about 0.1 mg, at least about 0.2 mg, at least about 0.3 mg, at least about 0.5 mg, at least about 1 mg, at least about 2 mg, at least about 3 mg, at least about 5 mg, at least about 10 mg, at least about 20 mg, at least about 30 mg, at least about 50 mg, at least about 100 mg, at least about 200 mg, at least about 300 mg, at least about 500 mg, at least about 1 g, at least about 2 g, at least about 3 g, at least about 5 g, at least about 10 g, etc. In some cases, the dosage may be no more than about 10 g, no more than about 5 g, no more than about 3 g, no more than about 2 g, no more than about 1 g, no more than about 500 mg, no more than about 300 mg, no more than about 200 mg, no more than about 100 mg, no more than about 50 mg, no more than about 30 mg, no more than about 20 mg, no more than about 10 mg, no more than about 5 mg, no more than about 3 mg, no more than about 2 mg, no more than about 1 mg, no more than about 0.5 mg, no more than about 0.3 mg, no more than about 0.2 mg, no more than about 0.1 mg, no more than about 0.05 mg, no more than about 0.03 mg, no more than about 0.02 mg, no more than about 0.01 mg, etc. In some cases, combinations of any of these are also possible, e.g., between about 0.01 mg and about 0.1 mg.

The compositions described herein can be used in combination therapy with one or more additional therapeutic agents. For combination treatment with more than one active agent, where the active agents are in separate dosage formulations, the active agents may be administered separately or in conjunction. In addition, the administration of one element may be prior to, concurrent to, or subsequent to the administration of the other agent. In certain embodiments, the additional therapeutic agent is present in a provided composition in addition to the compounds described herein. In other embodiments, the additional therapeutic agent is administered separately from the compositions described herein.

When co-administered with other agents, an "effective amount" of the second agent will depend on the type of drug used. Suitable dosages are known for approved agents and can be adjusted by the skilled artisan according to the condition of the subject, the type of condition(s) being treated and the amount of a compound described herein being used. In cases where no amount is expressly noted, an effective amount should be assumed.

In certain embodiments, a composition comprising compounds as described herein, and the additional therapeutic agent are each administered in an effective amount (i.e., each in an amount which would be therapeutically effective if administered alone). In other embodiments, a composition comprising compounds as described herein, and the additional therapeutic agent are each administered in an amount which alone does not provide a therapeutic effect (a sub-therapeutic dose). In yet other embodiments, a composition comprising compounds as described herein can be administered in an effective amount, while the additional therapeutic agent is administered in a sub-therapeutic dose. In still other embodiments, a composition comprising compounds as described herein can be administered in a sub-therapeutic dose, while the additional therapeutic agent is administered in an effective amount.

As used herein, the terms "in combination" or "co-administration" can be used interchangeably to refer to the use of more than one therapy (e.g., one or more prophylactic and/or therapeutic agents). The use of the terms does not restrict the order in which therapies (e.g., prophylactic and/or therapeutic agents) are administered to a subject.

Co-administration encompasses administration of the first and second amounts of the compounds in an essentially simultaneous manner, such as in a single pharmaceutical composition, for example, capsule or tablet having a fixed ratio of first and second amounts, or in multiple, separate capsules or tablets for each. In addition, such co-administration also encompasses use of each compound in a sequential manner in either order. When co-administration involves the separate administration of the first amount of a composition as described herein, and a second amount of an additional therapeutic agent, the compounds are administered sufficiently close in time to have the desired therapeutic effect. For example, the period of time between each administration which can result in the desired therapeutic effect, can range from minutes to hours and can be determined taking into account the properties of each compound. For example, a composition as described herein, and the second therapeutic agent can be administered in any order within about 24 hours of each other, within about 16 hours of each other, within about 8 hours of each other, within about 4 hours of each other, within about 1 hour of each other or within about 30 minutes of each other.

More specifically, a first therapy (e.g., a prophylactic or therapeutic agent such as a composition described herein)

can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy to a subject.

In one set of embodiments, a composition such as is discussed herein may be applied to the skin or mucosal surface of a subject, e.g., at any suitable location. The composition may be contacted using any suitable method. For example, the composition may be rubbed on, poured on, applied with an applicator (e.g., a gauze pad, a swab, a bandage, etc.), or the like. In some cases, the composition can be a liquid, a gel, a cream, a lotion, an ointment, a solid "stick," or the like, that can be applied to the skin or mucosal surface by hand, for example, by rubbing or spraying. The composition may be applied to any suitable surface of the subject, e.g., the head, neck, arms, or legs. In addition, in certain embodiments, the composition is applied to a mucosal surface of the subject. For example, the composition may be applied to the nose or nostrils, the mouth, the lips, the eyelids, the ears, the genital area (of either male or female subjects), or the anus.

The compositions may additionally comprise one or more adjunct ingredients, for instance, pharmaceutical drugs or skin care agents. For example, compositions may include adjuvants such as salts, buffering agents, diluents, excipients, chelating agents, fillers, drying agents, antioxidants, antimicrobials, preservatives, binding agents, bulking agents, silicas, solubilizers, or stabilizers. Non-limiting examples include species such as calcium carbonate, sodium carbonate, lactose, kaolin, calcium phosphate, or sodium phosphate; granulating and disintegrating agents such as corn starch or algenic acid; binding agents such as starch, gelatin or acacia; lubricating agents such as magnesium stearate, stearic acid, or talc; time-delay materials such as glycerol monostearate or glycerol distearate; suspending agents such as sodium carboxymethylcellulose, methylcellulose, hydroxypropylmethylcellulose, sodium alginate, polyvinylpyrrolidone; dispersing or wetting agents such as lecithin or naturally-occurring phosphatides; thickening agents such as cetyl alcohol or beeswax; buffering agents such as acetic acid and salts thereof, citric acid and salts thereof, boric acid and salts thereof, or phosphoric acid and salts thereof; or preservatives such as benzalkonium chloride, chlorobutanol, parabens, or thimerosal. Suitable concentrations can be determined by those of ordinary skill in the art, using no more than routine experimentation. Those of ordinary skill in the art will know of other suitable formulation ingredients, or will be able to ascertain such, using only routine experimentation.

Preparations can include sterile aqueous or nonaqueous solutions, suspensions and emulsions, which can be isotonic with the blood of the subject in certain embodiments. Examples of nonaqueous solvents are polypropylene glycol, polyethylene glycol, vegetable oil such as olive oil, sesame oil, coconut oil, arachis oil, peanut oil, mineral oil, organic esters such as ethyl oleate, or fixed oils including synthetic mono or di-glycerides. Aqueous solvents include water, alcoholic/aqueous solutions, emulsions or suspensions, including saline and buffered media. Parenteral vehicles include sodium chloride solution, 1,3-butandiol, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents and inert gases and the like. Those of skill in the art can readily determine the various parameters for preparing and formulating the compositions without resort to undue experimentation.

In some embodiments, a composition such as described herein may be applied to a surgical device, tool, or other substrate. For example, a composition may be applied to sutures, implants, surgical tools, or other substrates that may come into contact with wounded tissue (e.g., cut tissue) during surgery. In some embodiments, a composition may be provided as a cream or ointment as described in more detail herein. It also should be appreciated that certain compositions may be provided on surgical dressings, bandages, or other material that is to be contacted to a surgical wound.

In one set of embodiments, a composition such as is described herein may be applied to a material or substrate immediately prior to use on a subject. However, in some embodiments, a material or substrate may be prepared (e.g., packaged, stored, or otherwise prepared) to contain a composition prior to use. For example, prepackaged bandages or surgical devices, sutures, or implants may be prepared and packaged with a coating of a composition such as is described herein. Compositions may be used for human or other animal subjects.

In another aspect, the present disclosure is directed to a kit including one or more of the compositions discussed herein. A "kit," as used herein, typically defines a package or an assembly including one or more of the compositions, and/or other compositions, for example, as described herein. Each of the compositions of the kit may be provided in liquid form (e.g., in solution), or in solid form (e.g., a dried powder). In certain cases, some of the compositions may be constitutable or otherwise processable (e.g., to an active form), for example, by the addition of a suitable solvent or other species, which may or may not be provided with the kit. Examples of other compositions or components include, but are not limited to, solvents, surfactants, diluents, salts, buffers, chelating agents, fillers, antioxidants, binding agents, bulking agents, preservatives, drying agents, antimicrobials, needles, syringes, packaging materials, tubes, bottles, flasks, beakers, dishes, frits, filters, rings, clamps, wraps, patches, containers, and the like, for example, for using, administering, modifying, assembling, storing, packaging, preparing, mixing, diluting, and/or preserving the compositions components for a particular use, for example, to a sample and/or a subject.

A kit may, in some cases, include instructions in any form that are provided in connection with compositions such as those discussed herein in such a manner that one of ordinary skill in the art would recognize that the instructions are to be associated with the compositions. For instance, the instructions may include instructions for the use, modification, mixing, diluting, preserving, administering, assembly, storage, packaging, and/or preparation of the composition and/or other compositions associated with the kit. In some cases, the instructions may also include instructions for the delivery and/or administration of the compositions, for example, for a particular use, e.g., to a sample and/or a subject. The instructions may be provided in any form recognizable by one of ordinary skill in the art as a suitable vehicle for containing such instructions, for example, written or published, verbal, audible (e.g., telephonic), digital, optical, visual (e.g., videotape, DVD, etc.) or electronic communications (including Internet or web-based communications), provided in any manner.

The following documents are incorporated herein by reference: U.S. Pat. No. 8,668,937, issued Mar. 11, 2014, entitled "Topical Nitric Oxide Systems and Methods of Use Thereof"; U.S. Pat. No. 8,435,942, issued Apr. 26, 2006, entitled "Methods for Formulating Stabilized Insulin Compositions"; U.S. Pat. No. 7,182,956, issued Feb. 27, 2007, entitled "Stable Topical Drug Delivery Compositions"; U.S. Pat. No. 8,273,711, issued Sep. 25, 2012, entitled "Topical Drug Delivery Using Phosphatidylcholine"; U.S. patent application Ser. No. 13/801,402, filed Mar. 13, 2013, entitled "Systems and Methods for Delivery of Peptides"; U.S. patent application Ser. No. 13/801,446, filed Mar. 13, 2013, entitled "Treatment of Skin, Including Aging Skin, to Improve Appearance"; U.S. patent application Ser. No. 13/801,488, filed Mar. 13, 2013, entitled "Hair Treatment Systems and Methods Using Peptides and Other Compositions"; U.S. patent application Ser. No. 13/801,518, filed Mar. 13, 2013, entitled "Skin Tanning Using Peptides and Other Compositions"; U.S. patent application Ser. No. 13/801,543, filed Mar. 13, 2013, entitled "Topical Systems and Methods for Treating Sexual Dysfunction"; U.S. patent application Ser. No. 13/800,952, filed Mar. 13, 2013, entitled "Immune Modulation Using Peptides and Other Compositions"; U.S. patent application Ser. No. 13/801,013, filed Mar. 13, 2013, entitled "Cardiovascular Disease Treatment and Prevention"; U.S. patent application Ser. No. 13/801,061, filed Mar. 13, 2013, entitled "Wound Healing Using Topical Systems and Methods"; U.S. patent application Ser. No. 13/801,110, filed Mar. 13, 2013, entitled "Peptide Systems and Methods for Metabolic Conditions"; U.S. patent application Ser. No. 13/801,188, filed Mar. 13, 2013, entitled "Methods and Systems for Treating or Preventing Cancer"; U.S. patent application Ser. No. 13/801,240, filed Mar. 13, 2013, entitled "Compositions and Methods for Affecting Mood States"; U.S. patent application Ser. No. 13/801,298, filed Mar. 13, 2013, entitled "Improvement of Memory or Learning Using Peptide and Other Compositions"; U.S. patent application Ser. No. 13/801,345, filed Mar. 13, 2013, entitled "Brain and Neural Treatments Comprising Peptides and Other Compositions"; U.S. patent application Ser. No. 13/019,101, filed Feb. 1, 2011, entitled "Method of Delivering Stable Topical Drug Compositions"; U.S. patent application Ser. No. 13/926,688, filed Jun. 25, 2013, entitled "Topical Drug Delivery Using Phosphatidylcholine"; Int. Pat. Apl. Ser. No. PCT/US2014/025822, filed Mar. 13, 2014, entitled "Treatment of Skin, Including Aging Skin, to Improve Appearance"; Int. Pat. Apl. Ser. No. PCT/US2014/025913, filed Mar. 13, 2014, entitled "Immune Modulation Using Peptides and Other Compositions"; Int. Pat. Apl. Ser. No. PCT/US2014/025996, filed Mar. 13, 2014, entitled "Cardiovascular Disease Treatment and Prevention"; Int. Pat. Apl. Ser. No. PCT/US2014/025572, filed Mar. 13, 2014, entitled "Wound Healing Using Topical Systems and Methods"; Int. Pat. Apl. Ser. No. PCT/US2014/025630, filed Mar. 13, 2014, entitled "Peptide Systems and Methods for Metabolic Conditions"; Int. Pat. Apl. Ser. No. PCT/US2014/025758, filed Mar. 13, 2014, entitled "Methods and Systems for Treating or Preventing Cancer"; Int. Pat. Apl. Ser. No. PCT/US2014/025898, filed Mar. 13, 2014, entitled "Improvement of Memory or Learning Using Peptide and Other Compositions"; Int. Pat. Apl. Ser. No. PCT/US2014/025820, filed Mar. 13, 2014, entitled "Brain and Neural Treatments Comprising Peptides and Other Compositions"; and Int. Pat. Apl. Ser. No. PCT/US2014/025705, filed Mar. 13, 2014, entitled "Systems and Methods for Delivery of Peptides."

LIST OF SEQUENCES

Sequences of spadin analogs. Peptide sequences are presented using the one-letter nomenclature. Amino acids in L-configuration are shown in capital letters. Amino acids in D-configuration are shown as lowercase letters. "Ac" corresponds to acetyl groups, "—$NH_2$" to amide groups, and "—COOH" corresponds to carboxylic acid group.

```
Propeptide PE (1-44)
                                          (SEQ ID NO: 1)
NH2-QDRLDAPPPPAAPLPRWSGPIGVSWGLRAAAAGGAFPRGGOURWR
R-COOH Analog 1 (retroinverso of Propeptide PE 1-44)
                                          (SEQ ID NO: 2)
NH2-rrwrGGrpfaGGaaaarlGwsvGipGswrplpaappppadlrd q-Ac Analog 2 (Spadin-PE-12-28)
                                          (SEQ ID NO: 3)
NH2-APLPRWSGPIGVSWGLR-COOH Analog 3 (N-acetylation and inversion of Analog 2)
                                          (SEQ ID NO: 4)
NH2-RLGWSVGIPGSWRPLPA-Ac Analog 4 (retroinverso of Analog 2)
                                          (SEQ ID NO: 5)
NH2-rlGwsvGipGswrplpa-Ac Analog 5 (G/A substitution in Analog 2)
                                          (SEQ ID NO: 6)
NH2-APLPRWSAPIAVSWALR-COOH Analog 6 (retroinverso of Analog 5)
                                          (SEQ ID NO: 7)
NH2-rlawsvaipaswrplpa-COOH Analog 7 (cyclization of Analog 3)
                                          (SEQ ID NO: 8)
cyclic(RLGWSVGIPGSWRPLPA)

Analog 8 (cyclization of 2 sequences of Analog 3)
                                          (SEQ ID NO: 9)
cyclic(RLGWSVGIPGSWRPLPARLGWSVGIPGSWRPLPA)

Analog 9 (Spadin-PE-1-28)
                                          (SEQ ID NO: 10)
NH2-QDRLDAPPPPAAPLPRWSGPIGVSWGLR-COOH Analog 10 (retroinverso of Analog 9)
                                          (SEQ ID NO: 11)
NH2-rlGwsvGipGswrplpaappppadlrdq-Ac Analog 11 (Spadin-PE 22-28)
                                          (SEQ ID NO: 12)
NH2-GVSWGLR-COOH Analog 12 (Biotin labeled Analog 11)
                                          (SEQ ID NO: 13)
Biotin-NH2-GVSWGLR-COOH Analog 13 (G/A substitution Analog 11)
                                          (SEQ ID NO: 14)
NH2-AVSWGLR-COOH Analog 14 (Biotin labeled Analog 13)
                                          (SEQ ID NO: 15)
```

```
-continued
Biotin-NH2-AVSWGLR-COOH

Analog 15 (Spadin-PE-21-28)
                                        (SEQ ID NO: 16)
NH2-IGVSWGLR-COOH Analog 16 (retroinverso of Analog 15)
                                        (SEQ ID NO: 17)
NH2-rlGwsvGi-Ac Analog 17 (Spandin-PE-6-28)
                                        (SEQ ID NO: 18)
NH2-APPPPAAPLPRWSGPIGVSWGLR-COOH Analog 18 (retroinverso of Analog 17)
                                        (SEQ ID NO: 19)
NH2-rlGwsvGipGswrplpaappppa-Ac Analog 19 (Spandin-PE-12-27)
                                        (SEQ ID NO: 20)
NH2-APLPRWSGPIGVSWGL-COOH Analog 20 (retroinverso of Analog 19)
                                        (SEQ ID NO: 21)
NH2-lGwsvGipGswrplpa-Ac Analog 21 (Spandin-PE-14-25)
                                        (SEQ ID NO: 22)
NH2-LPRWSGPIGVSW-COOH Analog 22 (retroinverso of Analog 21)
                                        (SEQ ID NO: 23)
NH2-wsvGIpGswrpl-Ac Analog 23 (Spandin-PE-22-25)
                                        (SEQ ID NO: 24)
NH2-GVSW-COOH Analog 24 (Spandin-PE-22-27)
                                        (SEQ ID NO: 25)
NH2-GVSWGL-COOH
```

While several embodiments of the present disclosure have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present disclosure. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present disclosure is/are used. Those skilled in the art will recognize, or be able to ascertain using no more than routine experimentation, many equivalents to the specific embodiments of the disclosure described herein. It is, therefore, to be understood that the foregoing embodiments are presented by way of example only and that, within the scope of the appended claims and equivalents thereto, the disclosure may be practiced otherwise than as specifically described and claimed. The present disclosure is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

When the word "about" is used herein in reference to a number, it should be understood that still another embodiment of the disclosure includes that number not modified by the presence of the word "about."

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

SEQUENCE LISTING

```
Sequence total quantity: 25
SEQ ID NO: 1            moltype = AA  length = 46
FEATURE                 Location/Qualifiers
source                  1..46
                        mol_type = protein
                        organism = Synthetic construct
SEQUENCE: 1
QDRLDAPPPP AAPLPRWSGP IGVSWGLRAA AAGGAFPRGG OURWRR                          46

SEQ ID NO: 2            moltype = AA  length = 44
FEATURE                 Location/Qualifiers
source                  1..44
                        mol_type = protein
                        organism = Synthetic construct
SITE                    1
                        note = D-Arginine
SITE                    2
                        note = D-Arginine
SITE                    3
                        note = D-Tryptophan
SITE                    4
                        note = D-Arginine
SITE                    7
                        note = D-Arginine
SITE                    8
                        note = D-Proline
SITE                    9
                        note = D-Phenylalanine
SITE                    10
                        note = D-Alanine
SITE                    13..16
                        note = D-Alanine
SITE                    17
                        note = D-Arginine
SITE                    18
                        note = D-Leucine
SITE                    20
                        note = D-Tryptophan
SITE                    21
                        note = D-Serine
SITE                    22
                        note = D-Valine
SITE                    24
                        note = D-Isoleucine
SITE                    25
                        note = D-Proline
SITE                    27
                        note = D-Serine
SITE                    28
                        note = D-Tryptophan
SITE                    29
                        note = D-Arginine
SITE                    30
                        note = D-Proline
SITE                    31
                        note = D-Leucine
SITE                    32
                        note = D-Proline
SITE                    33..34
                        note = D-Alanine
SITE                    35..38
                        note = D-Proline
SITE                    39
                        note = D-Alanine
SITE                    40
                        note = D-Aspartic acid
```

```
SITE                    41
                        note = D-Leucine
SITE                    42
                        note = D-Arginine
SITE                    43
                        note = D-Aspartic acid
SITE                    44
                        note = D-Glutamine
SEQUENCE: 2
RRWRGGRPFA GGAAAARLGW SVGIPGSWRP LPAAPPPPAD LRDQ                44

SEQ ID NO: 3            moltype = AA   length = 17
FEATURE                 Location/Qualifiers
source                  1..17
                        mol_type = protein
                        organism = Synthetic construct
SEQUENCE: 3
APLPRWSGPI GVSWGLR                                              17

SEQ ID NO: 4            moltype = AA   length = 17
FEATURE                 Location/Qualifiers
source                  1..17
                        mol_type = protein
                        organism = Synthetic construct
SEQUENCE: 4
RLGWSVGIPG SWRPLPA                                              17

SEQ ID NO: 5            moltype = AA   length = 17
FEATURE                 Location/Qualifiers
source                  1..17
                        mol_type = protein
                        organism = Synthetic construct
SITE                    1
                        note = D-Arginine
SITE                    2
                        note = D-Leucine
SITE                    4
                        note = D-Tryptophan
SITE                    5
                        note = D-Serine
SITE                    6
                        note = D-Valine
SITE                    8
                        note = D-Isoleucine
SITE                    9
                        note = D-Proline
SITE                    11
                        note = D-Serine
SITE                    12
                        note = D-Tryptophan
SITE                    13
                        note = D-Arginine
SITE                    14
                        note = D-Proline
SITE                    15
                        note = D-Leucine
SITE                    16
                        note = D-Proline
SITE                    17
                        note = D-Alanine
SEQUENCE: 5
RLGWSVGIPG SWRPLPA                                              17

SEQ ID NO: 6            moltype = AA   length = 17
FEATURE                 Location/Qualifiers
source                  1..17
                        mol_type = protein
                        organism = Synthetic construct
SEQUENCE: 6
APLPRWSAPI AVSWALR                                              17

SEQ ID NO: 7            moltype = AA   length = 17
FEATURE                 Location/Qualifiers
source                  1..17
                        mol_type = protein
                        organism = Synthetic construct
SITE                    1
                        note = D-Arginine
SITE                    2
```

```
SITE            3
                note = D-Leucine
SITE            4
                note = D-Alanine
SITE            5
                note = D-Tryptophan
SITE            6
                note = D-Serine
SITE            7
                note = D-Valine
SITE            8
                note = D-Alanine
SITE            9
                note = D-Isoleucine
SITE            10
                note = D-Proline
SITE            11
                note = D-Alanine
SITE            12
                note = D-Serine
SITE            13
                note = D-Tryptophan
SITE            14
                note = D-Arginine
SITE            15
                note = D-Proline
SITE            16
                note = D-Leucine
SITE            17
                note = D-Proline
                note = D-Alanine
SEQUENCE: 7
RLAWSVAIPA SWRPLPA                                                    17

SEQ ID NO: 8    moltype = AA  length = 17
FEATURE         Location/Qualifiers
source          1..17
                mol_type = protein
                organism = Synthetic construct
REGION          1..17
                note = Cyclic peptide
SEQUENCE: 8
RLGWSVGIPG SWRPLPA                                                    17

SEQ ID NO: 9    moltype = AA  length = 34
FEATURE         Location/Qualifiers
source          1..34
                mol_type = protein
                organism = Synthetic construct
REGION          1..34
                note = Cyclic peptide
SEQUENCE: 9
RLGWSVGIPG SWRPLPARLG WSVGIPGSWR PLPA                                 34

SEQ ID NO: 10   moltype = AA  length = 28
FEATURE         Location/Qualifiers
source          1..28
                mol_type = protein
                organism = Synthetic construct
SEQUENCE: 10
QDRLDAPPPP AAPLPRWSGP IGVSWGLR                                        28

SEQ ID NO: 11   moltype = AA  length = 28
FEATURE         Location/Qualifiers
source          1..28
                mol_type = protein
                organism = Synthetic construct
SITE            1
                note = D-Arginine
SITE            2
                note = D-Leucine
SITE            4
                note = D-Tryptophan
SITE            5
                note = D-Serine
SITE            6
                note = D-Valine
SITE            8
                note = D-Isoleucine
```

| | | |
|---|---|---|
| SITE | 9 | |
| | note = D-Proline | |
| SITE | 11 | |
| | note = D-Serine | |
| SITE | 12 | |
| | note = D-Tryptophan | |
| SITE | 13 | |
| | note = D-Arginine | |
| SITE | 14 | |
| | note = D-Proline | |
| SITE | 15 | |
| | note = D-Leucine | |
| SITE | 16 | |
| | note = D-Proline | |
| SITE | 17 | |
| | note = D-Alanine | |
| SITE | 18 | |
| | note = D-Alanine | |
| SITE | 19 | |
| | note = D-Proline | |
| SITE | 20 | |
| | note = D-Proline | |
| SITE | 21 | |
| | note = D-Proline | |
| SITE | 22 | |
| | note = D-Proline | |
| SITE | 23 | |
| | note = D-Alanine | |
| SITE | 24 | |
| | note = D-Aspartic acid | |
| SITE | 25 | |
| | note = D-Leucine | |
| SITE | 26 | |
| | note = D-Arginine | |
| SITE | 27 | |
| | note = D-Aspartic acid | |
| SITE | 28 | |
| | note = D-Glutamine | |
| SEQUENCE: 11 | | |
| RLGWSVGIPG SWRPLPAAPP PPADLRDQ | | 28 |
| | | |
| SEQ ID NO: 12 | moltype = AA  length = 7 | |
| FEATURE | Location/Qualifiers | |
| source | 1..7 | |
| | mol_type = protein | |
| | organism = Synthetic construct | |
| SEQUENCE: 12 | | |
| GVSWGLR | | 7 |
| | | |
| SEQ ID NO: 13 | moltype = AA  length = 7 | |
| FEATURE | Location/Qualifiers | |
| source | 1..7 | |
| | mol_type = protein | |
| | organism = Synthetic construct | |
| SEQUENCE: 13 | | |
| GVSWGLR | | 7 |
| | | |
| SEQ ID NO: 14 | moltype = AA  length = 7 | |
| FEATURE | Location/Qualifiers | |
| source | 1..7 | |
| | mol_type = protein | |
| | organism = Synthetic construct | |
| SEQUENCE: 14 | | |
| AVSWGLR | | 7 |
| | | |
| SEQ ID NO: 15 | moltype = AA  length = 7 | |
| FEATURE | Location/Qualifiers | |
| source | 1..7 | |
| | mol_type = protein | |
| | organism = Synthetic construct | |
| SEQUENCE: 15 | | |
| AVSWGLR | | 7 |
| | | |
| SEQ ID NO: 16 | moltype = AA  length = 8 | |
| FEATURE | Location/Qualifiers | |
| source | 1..8 | |
| | mol_type = protein | |
| | organism = Synthetic construct | |
| SEQUENCE: 16 | | |

```
IGVSWGLR                                                                              8

SEQ ID NO: 17           moltype = AA  length = 8
FEATURE                 Location/Qualifiers
source                  1..8
                        mol_type = protein
                        organism = Synthetic construct
SITE                    1
                        note = D-Arginine
SITE                    2
                        note = D-Leucine
SITE                    4
                        note = D-Tryptophan
SITE                    5
                        note = D-Serine
SITE                    6
                        note = D-Valine
SITE                    8
                        note = D-Isoleucine
SEQUENCE: 17
RLGWSVGI                                                                              8

SEQ ID NO: 18           moltype = AA  length = 23
FEATURE                 Location/Qualifiers
source                  1..23
                        mol_type = protein
                        organism = Synthetic construct
SEQUENCE: 18
APPPPAAPLP RWSGPIGVSW GLR                                                            23

SEQ ID NO: 19           moltype = AA  length = 23
FEATURE                 Location/Qualifiers
source                  1..23
                        mol_type = protein
                        organism = Synthetic construct
SITE                    1
                        note = D-Arginine
SITE                    2
                        note = D-Leucine
SITE                    4
                        note = D-Tryptophan
SITE                    5
                        note = D-Serine
SITE                    6
                        note = D-Valine
SITE                    8
                        note = D-Isoleucine
SITE                    9
                        note = D-Proline
SITE                    11
                        note = D-Serine
SITE                    12
                        note = D-Tryptophan
SITE                    13
                        note = D-Arginine
SITE                    14
                        note = D-Proline
SITE                    15
                        note = D-Leucine
SITE                    16
                        note = D-Proline
SITE                    17
                        note = D-Alanine
SITE                    18
                        note = D-Alanine
SITE                    19
                        note = D-Proline
SITE                    20
                        note = D-Proline
SITE                    21
                        note = D-Proline
SITE                    22
                        note = D-Proline
SITE                    23
                        note = D-Alanine
SEQUENCE: 19
RLGWSVGIPG SWRPLPAAPP PPA                                                            23

SEQ ID NO: 20           moltype = AA  length = 16
```

```
                              -continued
FEATURE                 Location/Qualifiers
source                  1..16
                        mol_type = protein
                        organism = Synthetic construct
SEQUENCE: 20
APLPRWSGPI GVSWGL                                                       16

SEQ ID NO: 21           moltype = AA  length = 16
FEATURE                 Location/Qualifiers
source                  1..16
                        mol_type = protein
                        organism = Synthetic construct
SITE                    1
                        note = D-Leucine
SITE                    3
                        note = D-Tryptophan
SITE                    4
                        note = D-Serine
SITE                    5
                        note = D-Valine
SITE                    7
                        note = D-Isoleucine
SITE                    8
                        note = D-Proline
SITE                    10
                        note = D-Serine
SITE                    11
                        note = D-Tryptophan
SITE                    12
                        note = D-Arginine
SITE                    13
                        note = D-Proline
SITE                    14
                        note = D-Leucine
SITE                    15
                        note = D-Proline
SITE                    16
                        note = D-Alanine
SEQUENCE: 21
LGWSVGIPGS WRPLPA                                                       16

SEQ ID NO: 22           moltype = AA  length = 12
FEATURE                 Location/Qualifiers
source                  1..12
                        mol_type = protein
                        organism = Synthetic construct
SEQUENCE: 22
LPRWSGPIGV SW                                                           12

SEQ ID NO: 23           moltype = AA  length = 12
FEATURE                 Location/Qualifiers
source                  1..12
                        mol_type = protein
                        organism = Synthetic construct
SITE                    1
                        note = D-Tryptophan
SITE                    2
                        note = D-Serine
SITE                    3
                        note = D-Valine
SITE                    6
                        note = D-Proline
SITE                    8
                        note = D-Serine
SITE                    9
                        note = D-Tryptophan
SITE                    10
                        note = D-Arginine
SITE                    11
                        note = D-Proline
SITE                    12
                        note = D-Leucine
SEQUENCE: 23
WSVGIPGSWR PL                                                           12

SEQ ID NO: 24           moltype = AA  length = 4
FEATURE                 Location/Qualifiers
source                  1..4
                        mol_type = protein
```

```
                    organism = Synthetic construct
SEQUENCE: 24
GVSW                                                                              4

SEQ ID NO: 25       moltype = AA   length = 6
FEATURE             Location/Qualifiers
source              1..6
                    mol_type = protein
                    organism = Synthetic construct
SEQUENCE: 25
GVSWGL                                                                            6
```

What is claimed is:

1. A composition, comprising:
a transdermal formulation comprising lecithin, dihexa, lipoic acid, spadin peptide, and phenyl-N-tert-butylnitrone, wherein the transdermal formulation comprises a liquid crystal multilamellar lecithin structure.

2. The composition of claim 1, wherein the ratio of dihexa:lipoic acid:spadin peptide:phenyl-N-tert-butylnitrone is any ratio of weight percents that adds up to 100%.

3. The composition of claim 1, wherein the ratio of dihexa:lipoic acid is between 0.3:1 and 1:0.06.

4. The composition of claim 1, wherein the ratio of dihexa:spadin peptide is between 0.3:1 and 1:0.06.

5. The composition of claim 1, wherein the ratio of dihexa:phenyl-N-tert-butylnitrone is between 0.3:1 and 1:0.06.

6. The composition of claim 1, wherein the ratio of lipoic acid:spadin peptide is between 0:1 and 1:0.

7. The composition of claim 1, wherein the ratio of lipoic acid:phenyl-N-tert-butylnitrone is between 0:1 and 1:0.

8. The composition of claim 1, wherein the ratio of spadin peptide:phenyl-N-tert-butylnitrone is between 0:1 and 1:0.

9. The composition of claim 1, wherein the ratio of spadin peptide:phenyl-N-tert-butylnitrone is between 0.3:0.7 and 0.7:0.3.

10. The composition of claim 1, wherein the dihexa is present in the composition at between 0.25 wt % and 50 wt %.

11. The composition of claim 1, wherein the lipoic acid is present in the composition at between 0.25 wt % and 50 wt %.

12. The composition of claim 1, wherein the spadin peptide, or any fragment thereof, comprises an amino acid sequence that is at least 85%, at least 90%, at least 95%, at least 99%, at least 99.5%, or at least 99.8% identical to the amino acid sequence of SEQ ID NO: 12 (Analog 11).

13. The composition of claim 1, wherein the spadin peptide, or any fragment thereof, is a retroinverso analog of the spadin peptide, or fragment thereof.

14. The composition of claim 1, wherein the spadin peptide is present in the composition at between 0.25 wt % and 50 wt %.

15. The composition of claim 1, wherein the phenyl-N-tert-butylnitrone is present in the composition at between 0.25 wt % and 50 wt %.

16. The composition of claim 1, wherein the composition further comprises a benfotiamine.

17. The composition of claim 16, wherein the benfotiamine is present at least about 0.1% by weight.

18. The composition of claim 16, wherein the benfotiamine is present at least about 5% by weight.

19. A method, comprising:
applying, to the skin of a subject, a pharmaceutical composition comprising lecithin, dihexa, lipoic acid, spadin peptide, and phenyl-N-tert-butylnitrone, wherein the pharmaceutical composition comprises a liquid crystal multilamellar lecithin structure.

20. The method of claim 19, wherein the composition further comprises a benfotiamine.

* * * * *